(12) United States Patent
Boyle et al.

(10) Patent No.: US 7,449,489 B2
(45) Date of Patent: Nov. 11, 2008

(54) INDOLYLALKYLAMINO-METHYLIDENECARBAMATE DERIVATIVES USEFUL AS GNRH ANTAGONISTS

(75) Inventors: Francis Thomas Boyle, Macclesfield (GB); Robert Davies, Macclesfield (GB); Zbigniew Matusiak, Macclesfield (GB); Michael Wardleworth, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 510 days.

(21) Appl. No.: 10/524,986

(22) PCT Filed: Aug. 18, 2003

(86) PCT No.: PCT/GB03/03606

§ 371 (c)(1),
(2), (4) Date: Nov. 10, 2005

(87) PCT Pub. No.: WO2004/018420

PCT Pub. Date: Mar. 4, 2004

(65) Prior Publication Data

US 2006/0258710 A1    Nov. 16, 2006

(30) Foreign Application Priority Data

Aug. 21, 2002 (EP) .................... 0219472

(51) Int. Cl.
A61K 31/404 (2006.01)
C07D 209/04 (2006.01)

(52) U.S. Cl. .......... 514/419; 548/469; 548/494; 548/495; 514/415; 514/419; 546/268.1; 546/276.4; 544/336; 544/358; 544/359

(58) Field of Classification Search ........... 548/469, 548/494, 495; 514/415, 419; 544/336, 358; 544/359; 456/268.1, 276.4
See application file for complete search history.

(56) References Cited

U.S. PATENT DOCUMENTS 6,809,098 B2 * 10/2004 Wardleworth et al. .... 514/235.2

FOREIGN PATENT DOCUMENTS

| WO | 97/21435 | 6/1997 |
|---|---|---|
| WO | 97/21703 | 6/1997 |
| WO | WO 97/21435 A1 | 6/1997 |
| WO | WO 97/21703 A1 | 6/1997 |
| WO | WO 97/21704 A1 | 6/1997 |
| WO | WO 97/21707 A1 | 6/1997 |
| WO | WO 98/55116 A1 | 12/1998 |
| WO | WO 98/55119 A1 | 12/1998 |
| WO | WO 98/55123 A1 | 12/1998 |
| WO | WO 98/55470 A1 | 12/1998 |
| WO | WO 98/55479 A1 | 12/1998 |
| WO | 99/20599 | 4/1999 |
| WO | WO 99/20599 A1 | 4/1999 |
| WO | WO 99/21553 A1 | 5/1999 |
| WO | WO 99/21557 A1 | 5/1999 |
| WO | WO 99/41251 A1 | 8/1999 |
| WO | WO 99/41252 A1 | 8/1999 |
| WO | WO 99/51231 A1 | 10/1999 |
| WO | WO 99/51232 A1 | 10/1999 |
| WO | WO 99/51233 A1 | 10/1999 |
| WO | WO 99/51234 A1 | 10/1999 |
| WO | WO 99/51595 A1 | 10/1999 |
| WO | WO 99/51596 A1 | 10/1999 |
| WO | WO 00/04013 A1 | 1/2000 |
| WO | WO 00/53178 A1 | 8/2000 |
| WO | WO 00/53179 A1 | 8/2000 |
| WO | WO 00/53180 A1 | 8/2000 |
| WO | WO 00/53181 A1 | 8/2000 |
| WO | WO 00/53185 A1 | 8/2000 |
| WO | WO 00/53602 A1 | 8/2000 |
| WO | WO 02/66459 A1 | 8/2002 |
| WO | 02/092565 | 11/2002 |
| WO | WO 00/69433 A1 | 11/2002 |
| WO | WO 02/92565 A2 | 11/2002 |

OTHER PUBLICATIONS

Ashton et al 'Substituted Indole-5-carboxamides and -acetamides as Potent Nonpeptide GnRH Receptor Antagonist.' Bioorganic & Medicinal Chemistry Letters 2001, vol. 11, pp. 1723-1726.

Ashton et al 'Potent Nonpeptide GnHR Receptor Antagonists Derived from Substituted Indole-5-carboxamides and -acetamides Bearing a Pyridine Side-Chain Terminus.' Bioorganic & Medicinal Chemistry Letters 2001, vol. 11, pp. 1727-1731.

Ashton et al 'Orally Bioavailable, Indole-Based Nonpeptide GnHR Receptor Antagonists with High Potancy and Functional Activity.' Bioorganic and medicinal Chemistry Letters 2001, vol. 11, pp. 2597-2602.

(Continued)

*Primary Examiner*—Golam M Shameem

(57) ABSTRACT

The invention relates to a group of novel indole compounds of Formula (I): wherein: $R^1, R^2, R^4, R^6, R^{6a}, R^7, R^8, R^9, R^{10}$, and A are as defined in the specification, which are useful as gonadotrophin releasing hormone antagonists. The invention also relates to pharmaceutical formulations of said compounds, methods of treatment using said compounds and to processes for the preparation of said compounds.

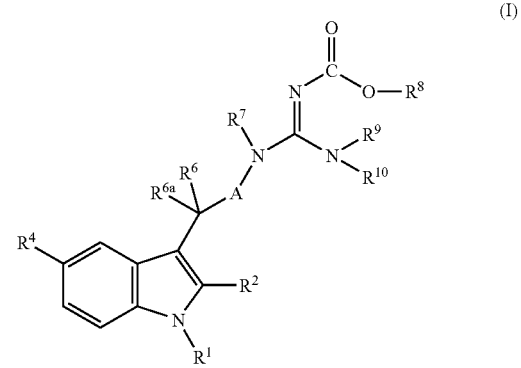

11 Claims, No Drawings

OTHER PUBLICATIONS

Chu et al. 'initial Structure-Activity Relationship of a Noval Class of Nonpeptidyl GnHR Receptor Antagonists: 2-Arylindoles.' Bioorganic and Medicinal Chemistry Letters 2001, vol. 11, pp. 509-513.

Chu et al. 'SAR Studies of novel 5-Substituted 2-Arylindoles as Nonpeptidyl GnHR Receptor Antagonists.' Bioorganic and Medicinal Chemistry Letters 2001, vol. 11, pp. 515-517.

Freidinger, R. M. 'Nonpeptide ligands for peptide and protein receptors.' Current Opinion in Chemical Biology 1999, vol. 3, pp. 395-406.

Goulet, M. T. 'Gonadotropin Releasing Hormone Antagonists.' Annual Reports in Medicinal Chemistry 1995, vol. 30, pp. 169-178.

Lin et al. '2-(3,5-Dimethylphenyl)tryptamine Derivatives That Bind to the GnHR Receptor.' Bioorganic & Medicinal Chemistry Letters 2001, vol. 11, pp. 1073-1076.

Lin et al. 'Heterocyclic Derivatives of 2-(3,5-Dimethylphenyl)tryptamine as GnHR Receptor Antagonists.' Bioorganic & Medicinal Chemistry Letters 2001, vol. 11, pp. 1077-1080.

Simoene, J. P. 'Synthesis of chiral β-methyl tryptamine-derived GnHR antagonists.' Tetrahedron Letters 2001, vol. 42, pp. 6459-6461.

Walsh et al. 'A convergent synthesis of (S)-β-methyl-2-aryltryptamine based gonadotropin releasing hormone antagonists.' Tetrahedron, 2001, vol. 57, pp. 5233-5241.

Young et al. '2-Arylindoles as Gonadotropin Releasing Hormone (GnHR) Antagonists: Optimization of the Tryptamine Side Chain.' Bioorganic & Medicinal Chemistry Letters, 2002, vol. 12, pp. 827-832.

Ujjainwalla, F. 'Total synthesis of 6- and 7-azaindole derived GnHR antagonists.' Tetrahedron Letters, 2001, vol. 42, pp. 6441-6445.

Simeone, J. P et al. 'Modification of the Pyridine Moiety of Nonpeptidyl Indole GnHR Receptor Antagonists.' Bioorganic & Medicinal Chemistry Letters, 2002, vol. 12, pp. 3329-3332.

Gibbs, J. B. 'Pharmaceutical Research in Molecular Onocology.' Cell, 1994, vol. 79, pp. 193-198.

* cited by examiner

INDOLYLALKYLAMINO-METHYLIDENECARBAMATE DERIVATIVES USEFUL AS GNRH ANTAGONISTS

CROSS-REFERENCE TO RELATED APPLICATIONS

This application is a US National Stage under 35 U.S.C § 371 of International Application No. PCT/GB2003/003606, filed Aug. 18, 2003, which claims priority under 35 U.S.C. § 119(a)-(d) to United Kingdom Patent Application No. 0219472.8 filed on Aug. 21, 2002, the specification of which is incorporated by reference herein.

The present invention relates to compounds which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

Gonadotropin releasing hormone (GnRH) is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known by other names, including gonadoliberin, LH releasing hormone (LHRH), FSH releasing hormone (FSH RH and LH/FSH releasing factor (LH/FSH RF).

GnRH plays an important role in regulating the action of LH and FSH (by regulation of their levels), and thus has a role in regulating the levels of gonadal steroids in both sexes, including the sex hormones progesterone, oestrogens and androgens. More discussion of GnRH can be found in WO 98/5519 and WO 97/14697, the disclosures of which are incorporated herein by reference.

It is believed that several diseases would benefit from the regulation of GnRH activity, in particular by antagonizing such activity. These include sex hormone related conditions such as sex hormone dependent cancer, benign prostatic hypertrophy and myoma of the uterus. Examples of sex hormone dependent cancers are prostatic cancer, uterine cancer, breast cancer and pituitary gonadotrophe adenoma.

The following disclose compounds purported to act as GnRH antagonists: WO 97/21435, WO 97/21703, WO 97/21704, WO 97/21707, WO 55116, WO 98/55119, WO 98/55123, WO 98/55470, WO 98/55479, WO 99/21553, WO 99/21557, WO 99/41251, WO 99/41252, WO 00/04013, WO 00/69433, WO 99/51231, WO 99/51232, WO 99/51233, WO 99/51234, WO 99/51595, WO 99/51596, WO 00/53178, WO 00/53180, WO 00/53179, WO 00/53181, WO 00/53185, WO 00/53602, WO 02/066477, WO 02/066478, WO 02/06645 and WO 02/092565.

It would be desirable to provide further compounds, such compounds being GnRH antagonists. Thus, according to the first aspect of the invention there is provided a compound of Formula (I),

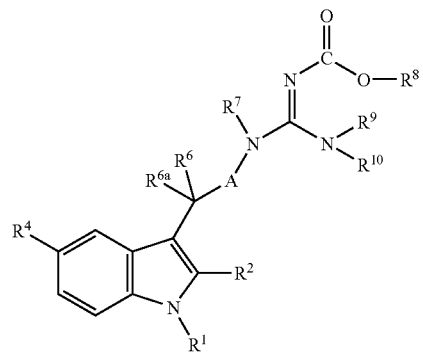

Formula (I)

wherein
A represents a direct bond or optionally substituted $C_{1-5}$alkylene;
$R^1$ represents hydrogen; optionally substituted $C_{1-8}$alkyl; or $(CH_2)_b$—$R^a$, wherein $R^a$ represents $C_{3-8}$cycloalkyl and b is zero or an integer from 1 to 6;
$R^2$ represents an optionally substituted mono- or bi-cyclic aromatic ring structure wherein the optional substituents are selected from cyano, $NR^3R^{3a}$, optionally substituted $C_{1-8}$alkyl, optionally substituted $C_{1-8}$alkoxy or halo;
$R^3$ and $R^{3a}$ are independently selected from hydrogen; optionally substituted $C_{1-8}$alkyl and optionally substituted aryl;
$R^4$ is selected from optionally substituted $C_{1-6}$alkoxy, an optionally substituted 3- to 8-membered heterocyclic ring containing from 1 to 4 heteroatoms independently selected from O, N and S; or a group of formula III-a; III-b; III-c; III-d; III-e; III-f, III-g, III-h, III-i, III-j or III-k;

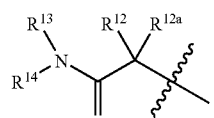

III-a

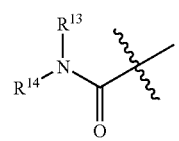

III-b

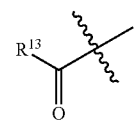

III-c

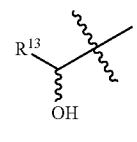

III-d

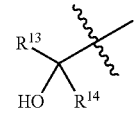

III-e

-continued

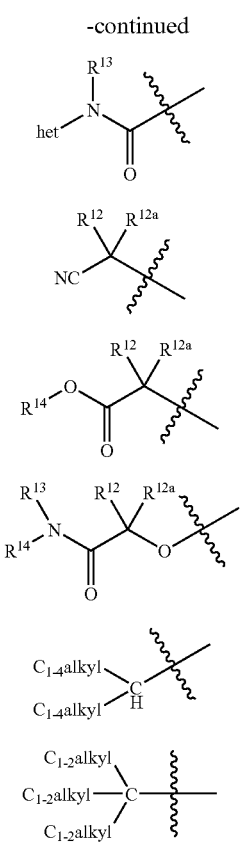

III-f

III-g

III-h

III-i

III-j

III-k wherein het represents an optionally substituted 3- to 8-membered heterocyclic ring containing from 1 to 4 heteroatoms independently selected from O, N and S;

$R^6$ and $R^{6a}$, are selected from:
(i) $R^6$ and $R^{6a}$ are independently selected from hydrogen and optionally substituted $C_{1-8}$alkyl; or
(ii) $R^6$ and $R^{6a}$ together represent carbonyl; or
(iii)

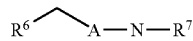

represents an optionally substituted 3- to 8-membered heterocyclic ring containing from 1 to 3 further heteroatoms independently selected from O, N and S, and $R^{6a}$ represents hydrogen and optionally substituted $C_{1-8}$alkyl;

$R^7$ represents hydrogen or optionally substituted $C_{1-8}$alkyl;

$R^8$ are selected from: $C_{1-4}$alkyl, $C_{2-4}$alkenyl, $C_{2-4}$alkynyl and heterocyclyl wherein $R^8$ is optionally substituted with halo, hydroxy, amino, $NO_2$, cyano, $C_{1-4}$alkanoyloxy, $N-C_{1-4}$alkylamino, $N,N$-di-$C_{1-4}$alkylamino, HO—$C_{2-4}$alkyl-NH—, HO—$C_{2-4}$alkyl-N($C_{1-4}$alkyl)—, —$S(O_n)$—$C_{1-4}$alkyl, —$N(R)S(O_n)$—$C_{1-4}$alkyl, —$S(O_n)N(R)$—$C_{1-4}$alkyl or heterocyclyl optionally substituted by $C_{1-4}$alkyl, $C_{2-4}$alkenyl or $C_{2-4}$alkynyl, wherein R is hydrogen or $C_{1-4}$alkyl;

$R^9$ is selected from:
(i) $R^9$ represents hydrogen, aryl, a 3- to 10 membered heterocyclic ring or optionally-substituted $C_{1-8}$alkyl; and (ii) the structure $N(R^9R^{10})$ represents an optionally-substituted 3- to 10 membered heterocyclic ring optionally containing from 1 to 3 further heteroatoms independently selected from O, N and S;

$R^{10}$ meets the definition in option (ii) for $R^9$ above or when $R^9$ meets the definition in option (i) above $R^{10}$ represents hydrogen or optionally substituted $C_{1-8}$alkyl;

$R^{12}$ and $R^{12a}$ are selected from:
(i) $R^{12}$ and $R^{12a}$ are independently selected from hydrogen or optionally substituted $C_{1-8}$alkyl; or
(ii) $R^{12}$ and $R^{12a}$ together with the carbon to which they are attached form an optionally substituted 3 to 7-membered cycloalkyl ring;

$R^{13}$ and $R^{14}$ are selected from:
(i) $R^{13}$ is selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8- membered heterocyclic ring optionally containing from 1 to 3 further heteroatoms independently selected from O, N and S; and $R^{14}$ is selected from hydrogen; optionally substituted $C_{1-8}$alkyl and optionally substituted aryl;
(ii) wherein $R^4$ represents a group of formula III-a, III-b or III-i, then the group $NR^{13}$(—$R^{14}$) represents an optionally substituted 3- to 8- membered heterocyclic ring optionally containing from 1 to 3 further heteroatoms independently selected from O, N and S; or
(iii) wherein $R^4$ represents structure III-e,

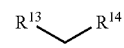

represents an optionally substituted 3- to 8- membered heterocyclic ring optionally containing from 1 to 4 heteroatoms independently selected from O, N and S;

n is 0 to 2;

or a salt, pro-drug or solvate thereof.

According to a further feature of the first aspect of the invention there is provided a pharmaceutical formulation comprising a compound of Formula (I), or salt, pro-drug or solvate thereof, and a pharmaceutically acceptable diluent or carrier.

According to a further feature of the first aspect of the invention there is provided the following uses of a compound of a compound of Formula (I), or salt, pro-drug or solvate thereof:
(a) the use in the manufacture of a medicament for antagonizing gonadotropin releasing hormone activity;
(b) the use in the manufacture of a medicament for administration to a patient, for reducing the secretion of luteinizing hormone by the pituitary gland of the patient; and
(c) the use in the manufacture of a medicament for administration to a patient, for therapeutically treating and/or preventing a sex hormone related condition in the patient, preferably a sex hormone related condition selected from prostate cancer and pre-menopausal breast cancer.

According to a further aspect of the invention there is provided a method of antagonizing gonadotropin releasing hormone activity in a patient, comprising administering a compound of Formula (I), or salt, pro-drug or solvate thereof, to a patient.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

Whilst the invention comprises compounds of the invention, and salts, pro-drugs or solvates thereof, in a further embodiment of the invention, the invention comprises compounds of the invention and salts thereof.

In the present specification, unless otherwise indicated, an alkyl, alkylene or alkenyl moiety may be linear or branched.

The term "alkylene" refers to the group —CH$_2$—. Thus, C$_8$ alkylene for example is —(CH$_2$)$_8$—.

The term "aryl" refers to phenyl or naphthyl.

The term "carbamoyl" refers to the group —CONH$_2$.

The term "halo" refers to fluoro, chloro, bromo or iodo.

The term "heterocyclyl" or "heterocyclic ring" refers to a 5-10 membered aromatic mono or bicyclic ring or a 5-10 membered saturated or partially saturated mono or bicyclic ring, said aromatic, saturated or partially unsaturated rings containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered aromatic heterocyclic rings include pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. A 9 or 10 membered bicyclic aromatic heterocyclic ring is an aromatic bicyclic ring system comprising a 6-membered ring fused to either a 5 membered ring or another 6 membered ring. Examples of 5/6 and 6/6 bicyclic ring systems include benzofuranyl, benzimidazolyl, benzthiophenyl, benzthiazolyl, benzisothiazolyl, benzoxazolyl, benzisoxazolyl, indolyl, pyridoimidazolyl, pyrimidoimidazolyl, quinolinyl, isoquinolinyl, quinoxalinyl, quinazolinyl, phthalazinyl, cinnolinyl and naphthyridinyl. Examples of saturated or partially saturated heterocyclic rings include pyrrolinyl, pyrrolidinyl, morpholinyl, piperidinyl, piperazinyl, dihydropyridinyl and dihydropyrimidinyl. This definition further comprises sulphur-containing rings wherein the sulphur atom has been oxidised to an S(O) or S(O2) group.

The term "aromatic ring" refers to a 5-10 membered aromatic mono or bicyclic ring optionally containing up to 5 heteroatoms independently selected from nitrogen, oxygen or sulphur. Examples of such "aromatic rings" include: phenyl, pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. Preferred aromatic rings include 'phenyl, thienyl and pyridyl.

The symbol

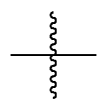

denotes where the respective group is linked to the remainder of the molecule.

For the avoidance of doubt, when

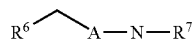

together form an optionally substituted 3- to 8- membered heterocyclic ring containing from 1 to 3 further heteroatoms independently selected from O, N and S, then the groups shown cyclise to form a nitrogen-containing heterocyclic ring, i.e

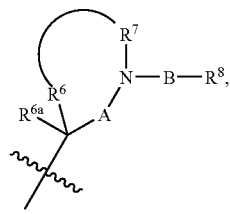

optionally containing from 1 to 3 further heteroatoms independently selected from O, N and S.

Examples of C$_{1-8}$alkyl include: methyl, ethyl, propyl, isopropyl, butyl, iso-butyl, tert-butyl and 2-methyl-pentyl; example of C$_{1-8}$alkylene include: methylene, ethylene and 2-methyl-propylene; examples of C$_{1-8}$alkoxy include methoxy, ethoxy and butyloxy; examples of C$_{1-4}$alkanoyloxy include formyloxy, propanoyloxy and butanoyloxy, examples of N—C$_{1-4}$alkylamino include N-methylamino and N-ethylamino; examples of N,N-di-C$_{1-4}$alkylamino, examples of HO—C$_{2-4}$alkyl-NH include hydroxymethylamino hydroxyethylamino and hydroxypropyamino, examples of HO—C$_{2-4}$alkyl-N(C$_{1-4}$alkyl) include N-methyl-hydroxymethylamino, N-ethyl-hydroxyethylamino, and N-propyl-hydroxypropyamino.

It is to be understood that, insofar as certain of the compounds of the invention may exist in optically active or racemic forms by virtue of one or more asymmetric carbon atoms, the invention includes in its definition any such optically active or racemic form which possesses the property of antagonizing gonadotropin releasing hormone (GnRH) activity. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of antagonizing gonadotropin releasing hormone (GnRH) activity.

It will also be understood that certain compounds of the present invention may exist in solvated, for example hydrated, as well as unsolvated forms. It is to be understood that the present invention encompasses all such solvated forms which possess the property of antagonizing gonadotropin releasing hormone (GnRH) activity.

Preferred compounds of Formula (I) are those wherein any one of the following or a combination of the following apply.

Preferably A represents optionally substituted C$_{1-5}$alkylene. Further preferably C$_{1-4}$alkylene. Most preferably methylene or ethylene.

Preferably R$^1$ represents hydrogen or optionally substituted C$_{1-6}$alkyl. More preferably R$^1$ represents hydrogen, methyl, ethyl or tert-butyl. Most preferably R$^1$ represents hydrogen.

Preferably R$^2$ represents an optionally substituted monocyclic aromatic ring structure wherein the optional substituents are selected from cyano, NR$^e$R$^f$, optionally substituted C$_{1-8}$alkyl (preferably, C$_{1-4}$alkyl, eg, methyl or ethyl), optionally substituted C$_{1-8}$alkoxy (preferably, C$_{1-6}$alkoxy, eg, methoxy, ethoxy or tert-butoxy) or halo (eg, F, Br or Cl) wherein R$^e$ and R$^f$ are independently selected from hydrogen, C$_{1-6}$alkyl or aryl. Further preferably R$^2$ is optionally substituted phenyl wherein the optional substituents are selected from cyano, $NR^eR^f$, optionally substituted $C_{1-4}$alkyl, optionally substituted $C_{1-6}$alkoxy, F, Br or Cl wherein $R^e$ and $R^f$ are as defined above. Yet further preferably $R^2$ is optionally substituted phenyl wherein the optional substituents are selected from methyl, ethyl, methoxy, ethoxy, tert-butoxy, F or Cl. Most preferably $R^2$ represents

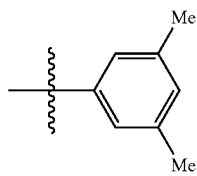

wherein Me represents methyl. Preferably $R^2$ bears 1, 2 or 3 substituents.

Preferably $R^3$ and $R^{3a}$ are independently selected from hydrogen; optionally substituted $C_{1-6}$alkyl and, optionally substituted aryl. Further preferably $R^3$ and $R^{3a}$ are independently selected from methyl, ethyl, tert-butyl and phenyl.

Preferably $R^4$ is selected from a group of formula III-a, III-g, III-h, III-i, III-j or III-k:

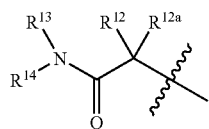
III-a

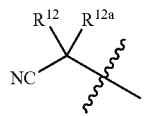
III-g

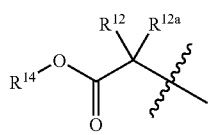
III-h

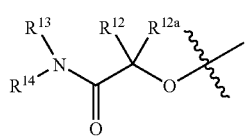
III-i

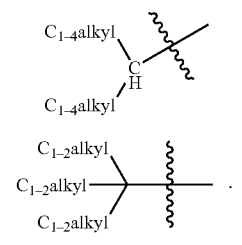
III-j

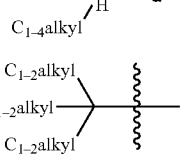
III-k

Further preferably $R^4$ is selected from one of the following groups:

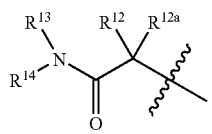
III-a

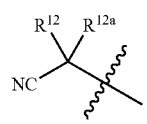
III-g

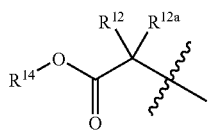
III-h

Yet further preferably $R^4$ is selected from one of the following groups:

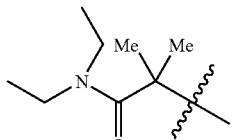

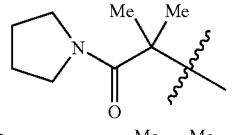

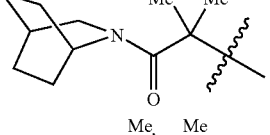

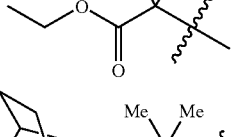

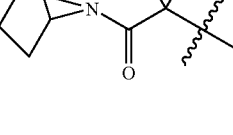

wherein Me represents methyl.

Most preferably $R^4$ is selected from one of the following groups:

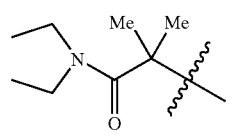

-continued

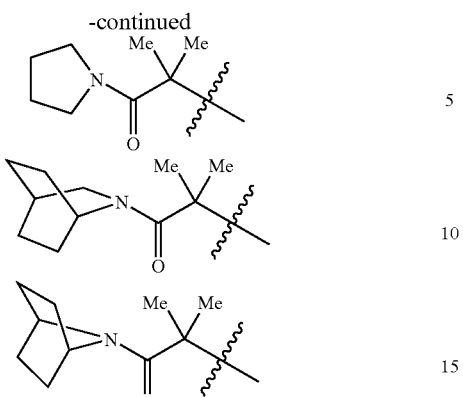

In one embodiment, $R^6$ and $R^{6a}$ each represent hydrogen and A represents $C_{1-4}$alkylene (preferably methylene).

In a further embodiment of the invention $R^6$ represents hydrogen, $R^{6a}$ represents methyl, and A represents $C_{1-4}$alkylene (preferably methylene).

Preferably $R^7$ is selected from hydrogen or optionally-substituted $C_{1-6}$alkyl. Further preferably $R^7$ represents hydrogen, methyl, ethyl or tert-butyl.

Preferably $R^8$ is selected from: $C_{1-4}$alkyl optionally substituted by heterocyclyl, $C_{1-4}$alkanoyloxy$C_{1-4}$alkyl or $C_{1-4}$alkanoyloxy, wherein heterocyclyl is optionally substituted by $C_{1-4}$alkyl. Preferably $C_{1-4}$alkyl or $C_{1-4}$alkyl substituted by heterocyclyl wherein heterocyclyl is optionally substituted by methyl or $C_{1-4}$alkanoylamino. Most preferably ethyl, isopropyl, n-butyl, 5-methyl-2-oxo-1,3-dioxol-4-ylmethyl or 1-oxoethoxy-(1,1,-dimethyl-ethyl).

Preferably $R^9$ comprise part of the heterocyclic ring formed by $N(R^9R^{10})$ or is hydrogen, optionally substituted aryl, an optionally substituted 3- to 10 membered heterocyclic ring or optionally substituted $C_{1-4}$alkyl wherein the optional substituents on $C_{1-4}$alkyl, aryl or a heterocyclic ring are selected from: hydroxy, amino, nitro, cyano, optionally-substituted aryl, optionally substituted 3- to 8- membered heterocyclyl containing from 1 to 4 heteroatoms independently selected from O, N and S, —O—$R^b$, C(O)NR$^b$R$^c$, —NR$^b$R$^c$, —NR$^c$C(O)—$R^b$, —C(O)NR$^b$R$^c$, —NR$^c$S(O$_{0-2}$)R$^b$, —S(O$_{0-2}$)R$^b$, wherein $R^b$ and $R^c$ are as defined above.

When $R^9$ is a $C_{1-6}$alkyl group substituted by an optionally-substituted 3 to 10 membered heterocyclic ring containing from 1 to 4 heteroatoms independently selected from O, N and S, the heterocyclic ring is preferably selected from pyridyl, thienyl, piperidinyl, imidazolyl, triazolyl, thiazolyl, pyrrolidinyl, piperazinyl, morpholinyl, imidazolinyl, benztriazolyl, benzimidazolyl, pyrimidinyl, pyrazinyl, pyridazinyl, oxazolyl, furanyl, pyrrolyl, 1,3-dioxolanyl, 2-azetinyl, each of which is optionally substituted. Further preferably a group of formula VI-a, VI-b, VI-c, VI-d, VI-e, VI-f, VI-g, VI-h, VI-i, VI-j or VI-k:, wherein each group is optionally substituted by one or more groups selected from $R^{16}$ on ring carbon atoms or ring heteroatoms where chemically feasible

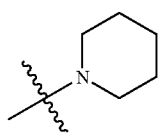

VI-a

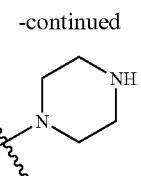

VI-b

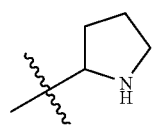

VI-c

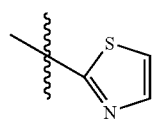

VI-d

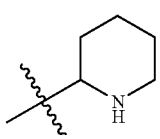

VI-e

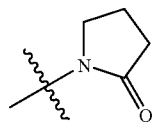

VI-f

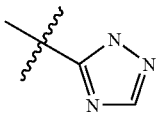

VI-g

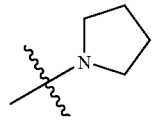

VI-h

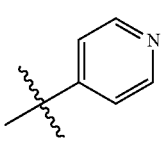

VI-i

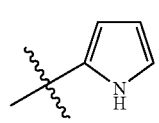

VI-j

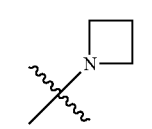

VI-k

Most preferably a group of formula VI-b, VI-i or VI-j:

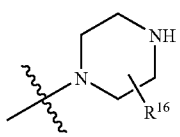

VI-b

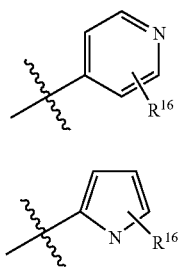

VI-i

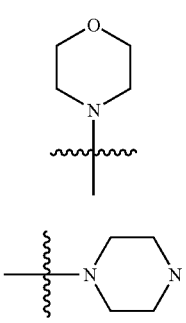

VI-j wherein $R^{16}$ represents hydrogen, aryl, a 3- to 10 membered heterocyclic ring or optionally substituted $C_{1-4}$alkyl wherein the optional substituents are selected from: hydroxy, amino, nitro, cyano, optionally-substituted phenyl, optionally substituted 3- to 8- membered heterocyclyl containing from 1 to 4 heteroatoms independently selected from O, N and S, —O—$R^b$, C(O)NR$^b$R$^c$, —NR$^b$R$^c$, —NR$^c$C(O)—R$^b$, —C(O)NR$^b$R$^c$, —NR$^c$S(O$_{0-2}$)R$^b$, —S(O$_{0-2}$)R$^b$, wherein $R^b$ and $R^c$ are as defined above;

In a further embodiment of the invention $R^9$ is $C_{1-4}$alkyl optionally substituted by cyano, preferably cyanopropyl.

Preferably $R^{10}$ comprises part of the heterocyclic ring formed by N(R$^9$R$^{10}$) or $R^{10}$ is hydrogen or optionally substituted $C_{1-6}$alkyl. Further preferably $R^{10}$ comprises part of the heterocyclic ring formed by N(R$^9$R$^{10}$) or $R^{10}$ is selected from: hydrogen, methyl, ethyl or iso-propyl. Most preferably $R^{10}$ is hydrogen or comprises part of the heterocyclic ring formed by N(R$^9$R$^{10}$).

When N(R$^9$R$^{10}$) represent an optionally substituted 3- to 10- membered heterocyclic ring, N(R$^9$R$^{10}$) is preferably selected from a 5- or 6-membered monocyclic ring containing between 1 and 3 (preferably 1 or 2) heteroatom independently selected from O, N and S. Further preferably a 5- or 6-membered monocyclic ring containing between 1 and 3 (preferably 1 or 2) heteroatom independently selected from O, N and S selected from pyrrolidinyl, thienyl, pyrazolidinyl, piperidinyl, morpholinyl, thiomorpholinyl piperazinyl, imidazole, azetidinyl or azetinyl. Further preferably the structure N(R$^9$R$^{10}$) is a heterocyclic ring selected from an optionally-substituted group of formula, IV-a, IV-b, IV-c, IV-d and IV-e, wherein the optional substituents are preferably selected from the groups listed for $R^{15}$ below

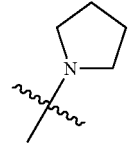

IV-a

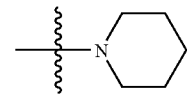

IV-b

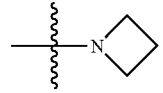

IV-c

IV-d

IV-e

Further preferably the structure N(R$^9$R$^{10}$) is selected from a group of formula Va, Vb, Vc or Vd:

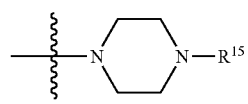

V-a

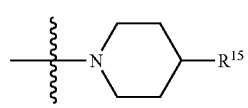

V-b

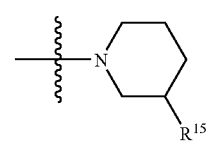

V-c

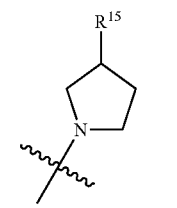

V-d

Most preferably the structure N(R$^9$R$^{10}$) is a group of formula V-c:

$R^{15}$ represents hydrogen, optionally substituted aryl, an optionally substituted 3- to 10 membered heterocyclic ring or optionally substituted $C_{1-4}$alkyl wherein the optional substituents on aryl, a heterocyclic ring or $C_{1-6}$alkyl are selected from: hydroxy, amino, nitro, cyano, optionally-substituted aryl, optionally substituted 3- to 8- membered heterocyclyl containing from 1 to 4 heteroatoms independently selected from O, N and S, —O—R$^b$, C(O)NR$^b$R$^c$, —NR$^b$R$^c$, —NR$^c$C(O)—R$^b$, —C(O)NR$^b$R$^c$, —NR$^c$S(O$_{0-2}$)R$^b$, —S(O$_{0-2}$)R$^b$, wherein $R^b$ and $R^c$ are as defined above. Preferably $R^{15}$ is heterocyclyl. Further preferably $R^{15}$ is selected from: pyridyl, pyrazinyl, pyridazinyl, pyrimidinyl or thiazolyl. Most preferably $R^{15}$ is pyridyl.

In a further embodiment of the invention $R^{15}$ is selected from pyridyl or $C_{1-4}$alkyl.

Further preferably pyridyl or methyl.

In a further embodiment of the invention $N(R^9R^{10})$ represent an optionally substituted 3- to 10- membered heterocyclic ring, wherein the optional substituents are selected from $R^{15}$ as defined above.

Preferably $R^{12}$ and $R^{12a}$ are independently selected from: hydrogen, optionally substituted $C_{1-6}$alkyl or $R^{12}$ and $R^{12a}$ together with carbon to which they are attached from an optionally substituted 3- to 6-membered cycloalkyl ring. Further preferably $R^{12}$ and $R^{12a}$ are independently selected from: hydrogen, methyl, ethyl or tert-butyl. Most preferably $R^{12}$ and $R^{12a}$ are both methyl.

Preferably $R^{13}$ and $R^{14}$, are independently selected from hydrogen, optionally substituted $C_{1-6}$alkyl, optionally substituted phenyl and —$R^d$-phenyl, where $R^d$ represents $C_{1-6}$alkylene or and an optionally substituted 3- to 8- membered heterocyclic ring (preferably, a 5- or 6-membered monocyclic ring) containing from 1 to 3 (preferably 1 or 2) further heteroatoms independently selected from O, N and S. Further preferably $R^{13}$ and $R^{14}$, are independently selected from hydrogen or $C_{1-6}$alkyl.

Where optional substitution is mentioned at various places, this refers to one, two, three or more optional substituents. Unless otherwise indicated above (ie, where a list of optional substituents is provided), each substituent can be independently selected from $C_{1-8}$alkyl (eg, $C_{2-6}$alkyl, and most preferably methyl, ethyl or tert-butyl); $C_{3-8}$cycloalkoxy, preferably cyclopropoxy, cyclobutoxy or cyclopentoxy; $C_{1-6}$alkoxy, preferably methoxy or $C_{2-4}$alkoxy; halo, preferably Cl or F; $Hal_3C$—, $Hal_2CH$—, $HalCH_2$—, $Hal_3CO$—, $Hal_2CHO$ or $Hal\,CH_2O$, wherein Hal represents halo (preferably F); $R^gCH_2O$—, $R^hC(O)N(R)$—, $R^hSO_2N(R)$— or $R^g$—$R^hN$—, wherein $R^g$ and $R^h$ independently represent hydrogen or $C_{1-8}$alkyl (preferably methyl or $C_{2-6}$ alkyl or $C_{2-4}$alkyl), or $R^g$—$R^hN$— represents an optionally substituted $C_{3-8}$, preferably $C_{3-6}$, heterocyclic ring optionally containing from 1 to 3 further heteroatoms independently selected from O, N and S; hydrogen; or $R^kC(O)O$— or $R^kC(O)$—, $R^k$ representing hydrogen, optionally substituted phenyl or $C_{1-6}$alkyl (preferably methyl, ethyl, iso-propyl or tert-butyl). For optional substitution of the heterocyclic ring represented by $R^g$—$R^hN$—, at least one (eg, one, two or three) substituents may be provided independently selected from $C_{1-6}$alkyl (eg, $C_{2-4}$alkyl, more preferably methyl); phenyl; $CF_3O$—; $F_2CHO$—; $C_{1-8}$alkoxy, preferably methoxy, ethoxy or $C_{3-6}$alkoxy; $C_{1-8}$alkoxyC(O), preferably methoxycarbonyl, ethoxycarbonyl, tert-butoxycarbonyl or $C_{3-6}$alkoxyC(O)—; phenoxycarbonyl; phenoxy; $C_{1-8}$alkanoyl, preferably acetyl, ethanoyl or $C_{3-6}$alkyanoyl; carboxy; $C_{1-8}$alkylS(O)$_{nn}$ wherein nn is an integer between 0 and 2, preferably methylthio, ethylthio, $C_{3-6}$alkylthio, methylsulphinyl, ethylsulphinyl, $C_{3-6}$alkylsulphinyl, methylsulphonyl, ethylsulphonyl or $C_{3-6}$alkylsulphonyl; hydroxy; halo (eg, F, Cl or Br); $R^mR^nN$— where $R^m$ and $R^n$ are independently hydrogen or $C_{1-6}$alkyl (preferably $C_{2-4}$alkyl, more preferably methyl, most preferably $R^m$=$R^n$=methyl); and nitro.

Where optional substitution of a ring is mentioned at various places, this most preferably refers to one, two, three or more substituents selected from $C_{1-8}$alkyl (eg, $C_{2-6}$alkyl, and most preferably methyl); $C_{1-8}$alkoxy, preferably methoxy, ethoxy or $C_{3-6}$alkoxy; $C_{1-8}$alkylS(O)$_{nn}$ wherein nn is an integer between 0 and 2, preferably methylthio, ethylthio, $C_{3-6}$alkylthio, methylsulphinyl, ethylsulphinyl, $C_{3-6}$alkylsulphinyl, methylsulphonyl, ethylsulphonyl or $C_{3-6}$alkylsulphonyl; halo (eg, F, Cl or Br); cyano; and $NO_2$. A preferred group of compounds of the invention comprise compounds of Formula (I) wherein:

$N(R^9R^{10})$ represents an optionally-substituted 3- to 8- membered heterocyclic ring optionally containing from 1 to 3 further heteroatoms independently selected from O, N and S, preferably substituted by heterocyclyl;

or a salt, pro-drug or solvate thereof.

A preferred group of compounds of the invention comprise compounds of Formula (I) wherein:

$R^9$ is a $C_{1-6}$alkyl group substituted by an optionally-substituted 3 to 8 membered heterocyclic ring containing from 1 to 4 heteroatoms independently selected from O, N and S; and $R^{10}$ represents hydrogen or $C_{1-6}$alkyl or a salt, pro-drug or solvate thereof.

A preferred group of compounds of the invention comprises a compound of Formula (Ia):

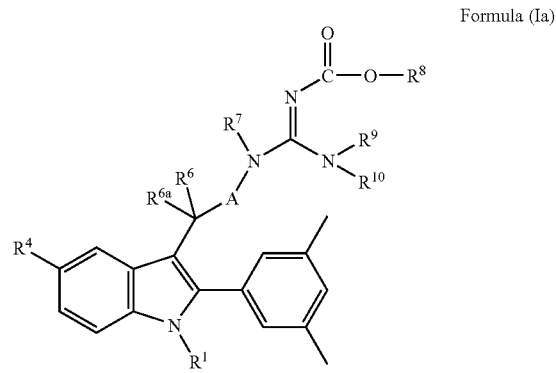

Formula (Ia)

wherein:

A, X, $R^1$, $R^2$, $R^3$, $R^{3a}$, $R^6$, $R^{6a}$, $R^7$, $R^8$, $R^9$, $R^{10}$, $R^{12}$ and $R^{12a}$ are as defined above;

or a salt, pro-drug or solvate thereof.

A preferred group of compounds of the invention comprises a compound of Formula (Ib):

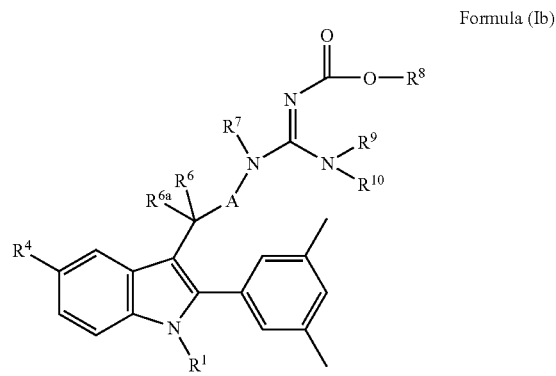

Formula (Ib)

wherein:

$R^4$ is selected from one of the following groups:

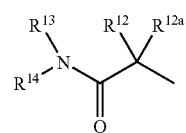
III-a

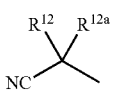
III-g

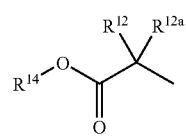
III-h

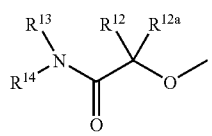
III-i

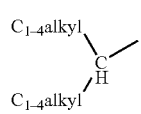
III-j

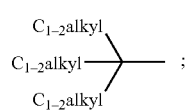
III-k and A, X, $R^1$, $R^3$, $R^{3a}$, $R^6$, $R^{6a}$, $R^7$, $R^8$, $R^9$, $R^{10}$, $R^{12}$, $R^{12a}$, $R^{13}$, and $R^{14}$ are as defined above; or a salt, pro drug or solvate thereof.

A further preferred group of compounds of the invention comprises a compound of Formula (Ic):

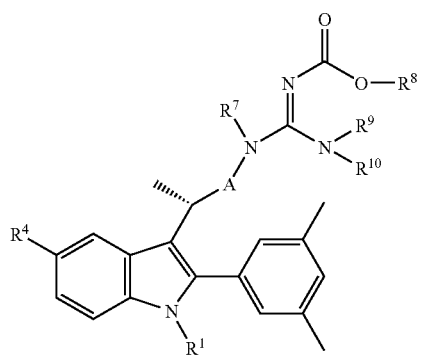
Formula (Ic)

wherein:

$R^4$ is selected from one of the following groups:

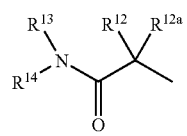
III-a

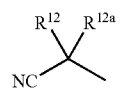
III-g

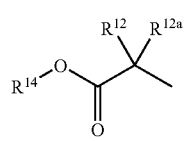
III-h

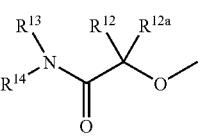
III-i

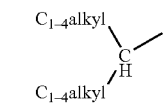
III-j

-continued

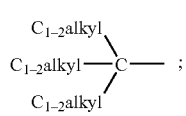
III-k and A, X, $R^1$, $R^2$, $R^3$, $R^{3a}$, $R^6$, $R^{6a}$, $R^7$, $R^8$, $R^9$, $R^{10}$, $R^{12}$, $R^{12a}$, $R^{13}$, and $R^{14}$ are as defined above;

or a salt, pro-drug or solvate thereof.

A yet further preferred group of compounds of the invention comprises a compound of Formula (Ia), (Ib) or (Ic) wherein:

$R^4$ is a group of Formula IIIa:

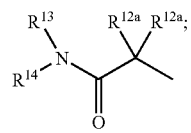
IIIa $NR^{13}(\text{—}R^{14})$ represents an optionally substituted 7- to 8-membered bicyclic heterocyclic ring and A, X, $R^1$, $R^2$, $R^3$, $R^{3a}$, $R^4$, $R^6$, $R^{6a}$, $R^7$, $R^8$, $R^9$, $R^{10}$, $R^{12}$ and $R^{12a}$ are as defined above; or a salt, pro-drug or solvate thereof.

Particularly preferred compounds according to the present invention are wherein the compound is selected from:

isopropyl [(1E)-({(2S)-2-[5-[2-(2-azabicyclo[2.2.2]oct-2-yl)-1,1-dimethyl-2-oxoethyl]-2-(3,5-dimethylphenyl)-1H-indol-3-yl]propyl}amino)(3-pyridin-4-ylpyrrolidin-1-yl)methylene]carbamate;

isopropyl [(1E)-({(2S)-2-[5-[2-(7-azabicyclo[2.2.1]hept-7-yl)-1,1-dimethyl-2-oxoethyl]-2-(3,5-dimethylphenyl)-1H-indol-3-yl]propyl}amino)(3-pyridin-4-ylpyrrolidin-1-yl)methylene]carbamate; and 2-[({[(1E)-({(2S)-2-[5-[2-(2-azabicyclo[2.2.2]oct-2-yl)-1,1-dimethyl-2-oxoethyl]-2-(3,5-dimethylphenyl)-1H-indol-3-yl]propyl}amino)(3-pyridin-4-ylpyrrolidin-1-yl)methylene]amino}carbonyl)oxy]-2-methylpropyl acetate or a salt, pro-drug or solvate thereof.

According to a further feature of the first aspect of the invention there is provided a pharmaceutical formulation comprising a compound of Formula (Ia), Formula (Ib), Formula (Ic) or preferred compounds of the invention, or salt, pro-drug or solvate thereof, and a pharmaceutically acceptable diluent or carrier.

According to a further feature of the first aspect of the invention there is provided the following uses of a compound of Formula (Ia), Formula (Ib), Formula (Ic) or preferred compounds of the invention, or salt, prodrug or solvate thereof:

(a) the use in the manufacture of a medicament for antagonising gonadotropin releasing hormone activity;

(b) the use in the manufacture of a medicament for administration to a patient, for reducing the secretion of luteinizing hormone by the pituitary gland of the patient; and (c) the use in the manufacture of a medicament for administration to a patient, for therapeutically treating and/or preventing a sex hormone related condition in the patient, preferably a sex hormone related condition selected from prostate cancer and pre-menopausal breast cancer.

The compounds of Formula (I) may be administered in the form of a pro-drug which is broken down in the human or animal body to give a compound of the Formula (I). Examples of pro-drugs include in-vivo hydrolysable esters of a compound of the Formula (I). Various forms of pro-drugs are known in the art. For examples of such pro-drug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the Formula (I) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the Formula (I) containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of Formula (I) can be prepared by a process comprising a step selected from (a) to (b) as follows, these processes are provided as a further feature of the invention:—

(a) Reaction of a compound of formula XXXII as follows

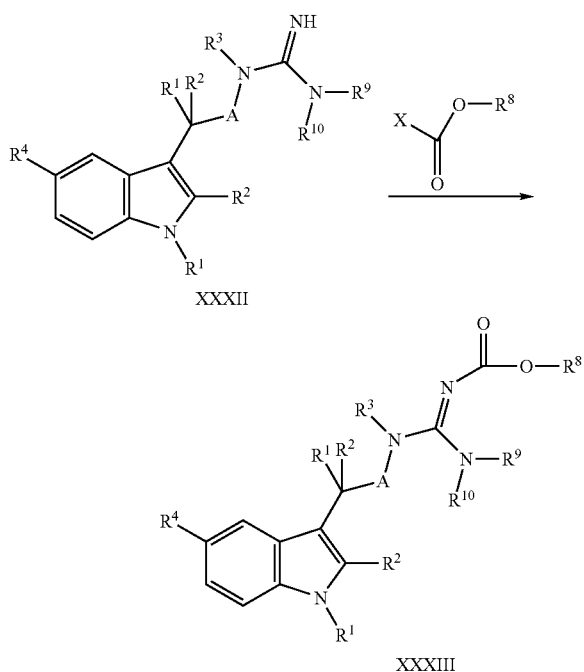

wherein X is a leaving group;

(b) Reaction of a compound of Formula XXXIV as follows

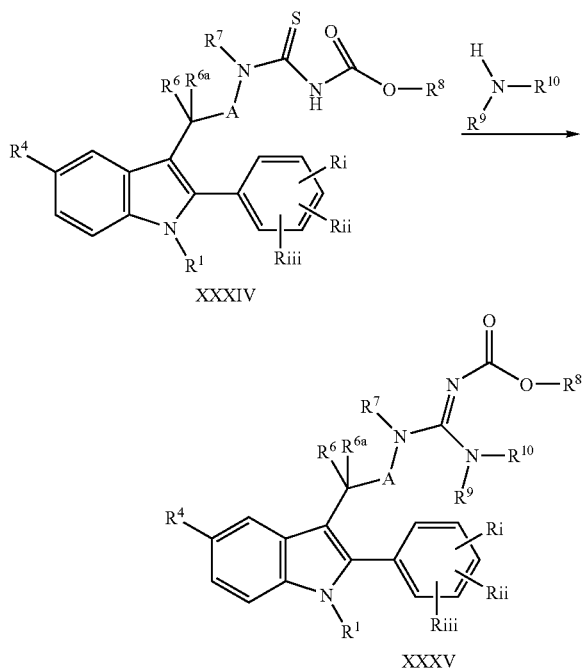

and thereafter if necessary:
i) converting a compound of the Formula (I) into another compound of the Formula (I);
ii) removing any protecting groups;
iii) forming a salt, pro-drug or solvate.

It will be appreciated by those skilled in the art that in the processes of the present invention certain functional groups such as hydroxyl or amino groups in the starting reagents or intermediate compounds may need to be protected by protecting groups. Thus, the preparation of the compounds of Formula (I) may involve, at an appropriate stage, the addition and subsequent removal of one or more protecting groups.

The protection and de-protection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The de-protection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The de-protection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

EXPERIMENTAL

GENERAL REACTION SCHEMES

In the following schemes wherein Ri, Rii and Riii represent optional substituents on the phenyl ring which are optionally protected as necessary and R represents a protecting group, group $R^2$ has been depicted as substituted phenyl for illustration purposes only. Other definitions of $R^2$ are also appropriate.

Scheme a.- Fisher indole synthesis.

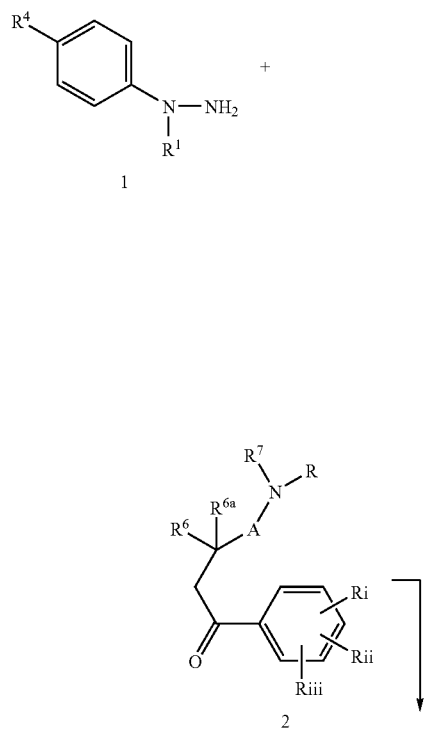

Tryptamines, such as 3 can be synthesised by the classic Fisher indole synthesis reaction by the condensation of a hydrazine 1 and a ketone 2, bearing hydrogen atoms α to the carbonyl (Scheme a). Treatment of these reactants in a suitable solvent, such as acetic acid, ethanol, tert-butanol, toluene, in the presence of an acid, such as sulphuric, hydrochloric, polyphosphoric and/or a Lewis acid, for example, boron trifluoride, zinc chloride, magnesium bromide, at elevated temperatures (for example 100° C.), gives the desired product. R represents a protecting group, eg tert-butylcarbamate or phthalimide.

Scheme b

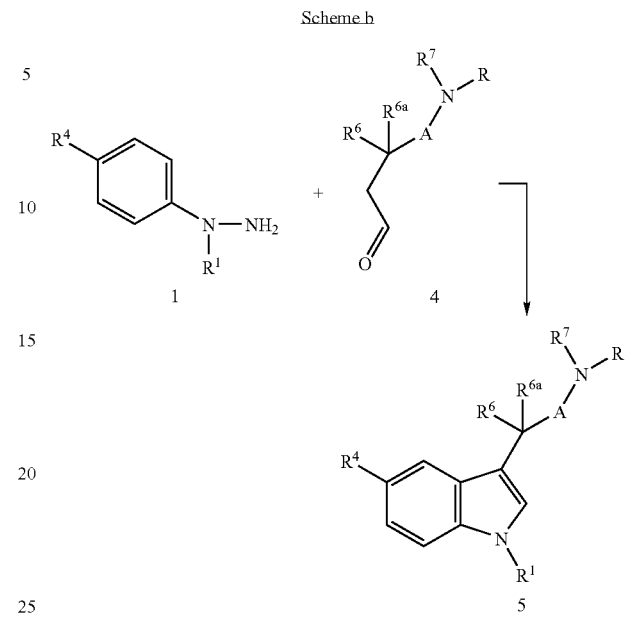

Tryptamines, such as represented in structure 5, can also be made using aldehydes 4, bearing hydrogen atoms α to the carbonyl, by cyclization using the conditions above. In this case the substituent at the 2-position must be added later (see scheme d).

Scheme c

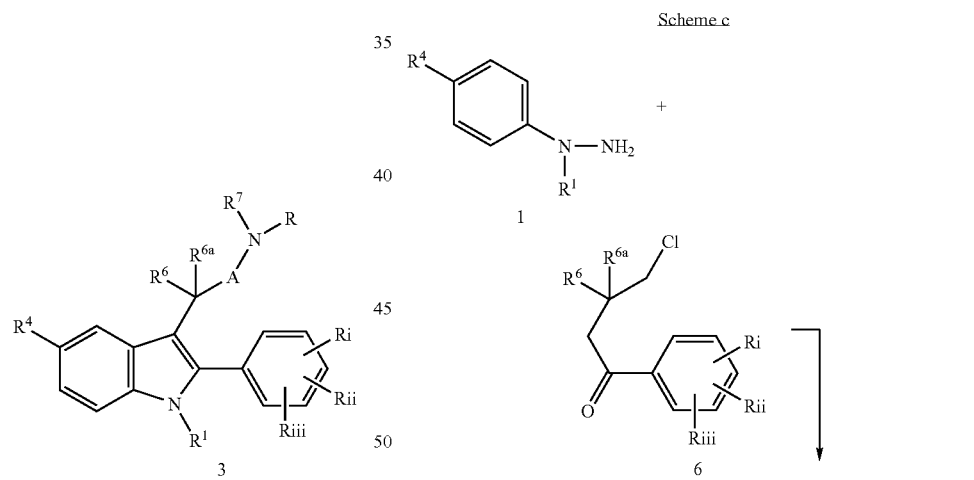

Tryptamine may also be synthesised utilising the Granburg reaction, wherein a hyradazine 1 is mixed with ketone 6, bearing a chlorine atom γ to the carbonyl, and heated in a suitable solvent such as ethanol, tert-butanol, toluene at a temperature between 50° C. and 120° C. (Scheme c).

Scheme d

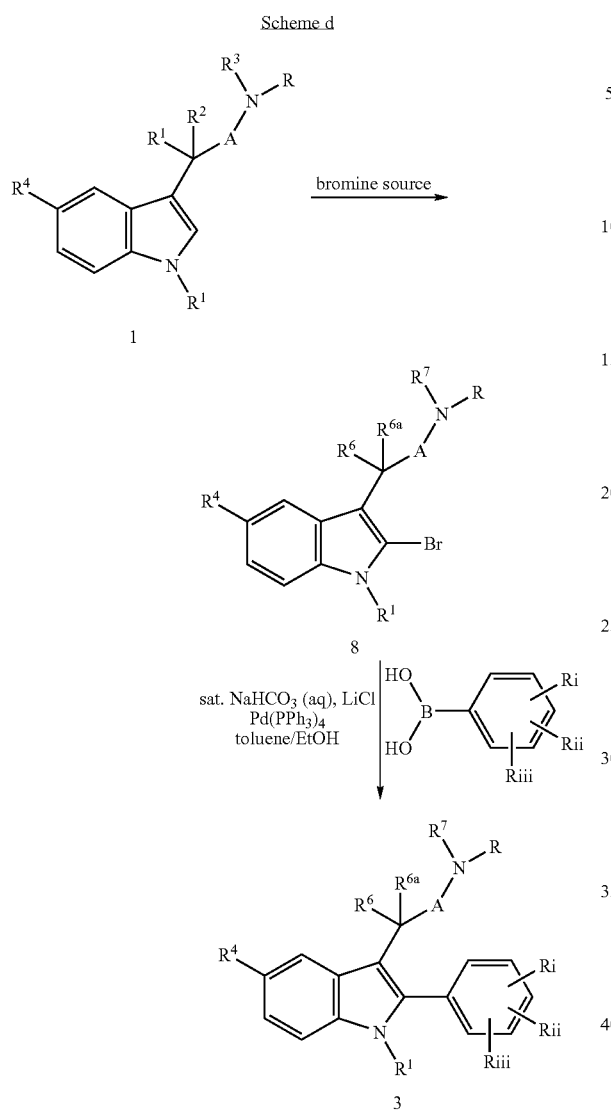

The tryptamine 5 can be treated with a 'bromine source', such as molecular bromide, pyridinium tribromide, pyrrolidone hydrobromide or polymer supported reagent equivalents, in an inert solvent such as chloroform, methylene chloride at −10° C. to 25° C. to yield the 2-bromo compound 8 (Scheme d). Reaction under Suzuki conditions with a palladium(0) catalyst, a weak base such aqueous sodium carbonate or saturated sodium hydrogen carbonate and the like, and a substituted aryl boronic acid from commercial sources or prepared (as described in: Gronowitz, S.; Hornfeldt, A.-B.; Yang, Y.,-H *Chem. Sci.* 1986, 26, 311-314), in an inert solvent such as toluene, benzene, dioxane, THF, DMF and the like, with heating between 25° C. and 100° C., preferably 80° C., for a period of 1-12 hours, to give the desired compound 3.

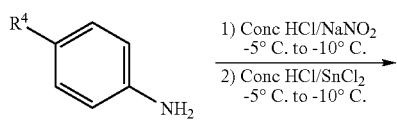

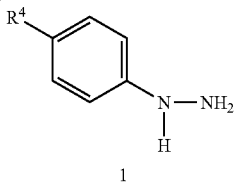

The hydrazines 1 can be purchased from commercial sources either as a free base or suitable salt (e.g. hydrochloride), which are both acceptable under the reaction conditions. Hydrazines may be synthesised by the two-step process of diazotisation of an aniline, under the preferred conditions of concentrated hydrochloric acid sodium nitrite at a temperature between −10° C. and −5° C., then reduction under the preferred conditions of tin(II) chloride in concentrated hydrochloric acid at a temperature between −10° C. and −5° C.

Scheme e.

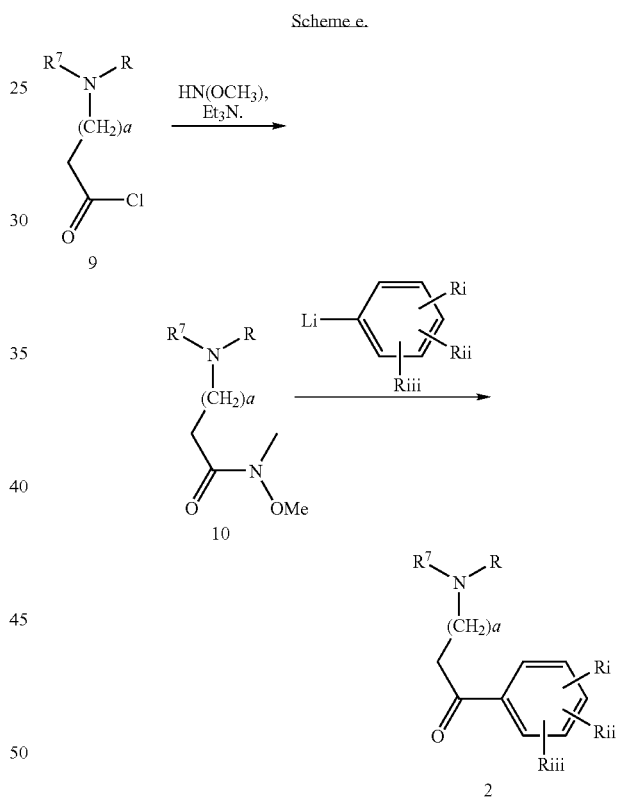

Substituted ketones 2 can be prepared, as outlined in Scheme e starting from appropriate acid chlorides such as 9. Treatment of the acid chloride with N,N-dimethylhydroxylamine hydrochloride in the presence of an amine base such as triethylamine, and a suitable solvent such as methylene chloride at a temperature of −10° C. to 25° C., yields the amide 10. Further reaction with a substituted aryl organolithium (prepared essentially as described in Wakefield B, J.; *Organolithium Methods* Academic Press Limited, 1988, pp. 27-29 and references therein) in an inert solvent such as tetrahydrofuran, diethyl ether, benzene, toluene or mixture thereof and the like, at a temperature between −100° C. and 0° C. then quenching of the reaction mixture with a mineral acid such as hydrochloric acid, yields the aryl ketone 2.

Scheme f.

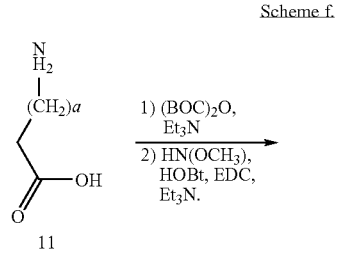

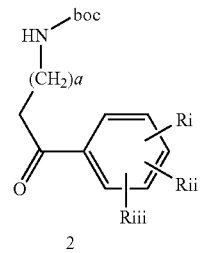

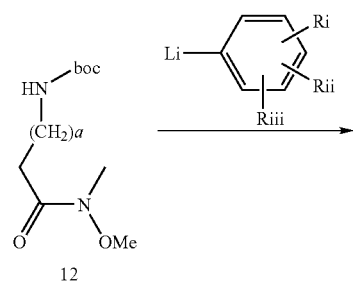

Commencing with a readily available amino acid with a suitable chain length[a]11, the nitrogen atom can be brought in at the beginning of the synthesis by the route shown in Scheme f. Protection of the amine group of 11 with a tert-butylcarbamate group is achieved by condensation with di-tert-butyl di-carbonate in the presence of an amine base, for example triethylamine, in an inert solvent such as methylene chloride, chloroform, benzene, toluene, tetrahydrofuran and mixtures thereof and the like, at a temperature of −10° C. to 25° C. Coupling of the acid product with N,N-dimethylhydroxylamine in the presence of a coupling reagent 1-(3-dimethylaminopropyl)-3-ethylcarbodiimide hydrochloride (EDC) or 1,3-dicyclohexylcarbodiimide (DCC) or the like, with or without 1-hydroxybenotriazole (HOBt), and suitable amine base, such as triethylamine and the like, in an inert solvent such as methylene chloride, chloroform, dimethylformamide, or mixture thereof, at or near room temperature for a period of 3 to 24 hours provided the corresponding coupled product 12. Following the same route described above for scheme d, the aryl group can then be installed.

Scheme g.

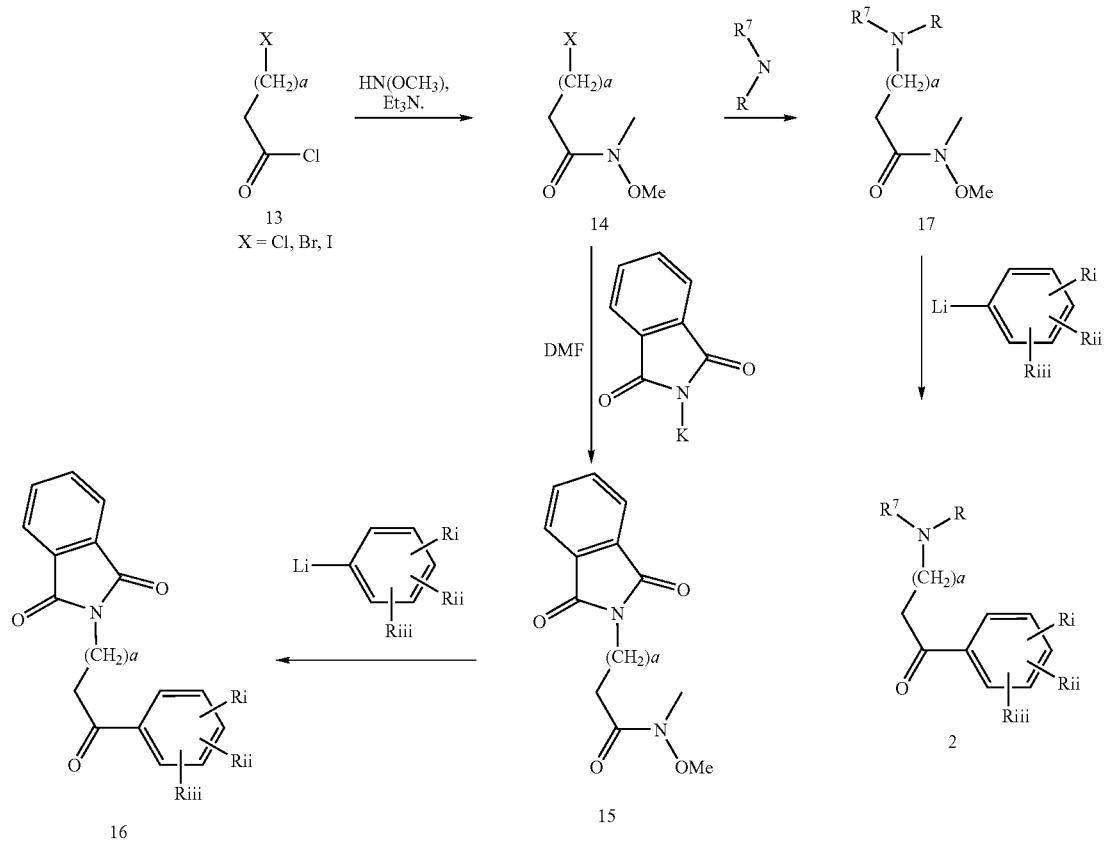

Scheme g illustrates another method for the synthesis of ketone such as 2 and 16, where the nitrogen group is introduced at a latter stage. As above a Weinreb amide 14 can be synthesised from an acid chloride. Treatment with the required amine, in an inert solvent such as THF, toluene, water and the such like can displace the group X to give 17. As above the aryl group can be introduced by displacement of the Weinreb amide with a suitable aryl lithium nucleophile. Alternatively the nitrogen atom can be introduced already protected as a phthalimide by displacement of the group x by potassium phthaliride, or similar salt thereof, by heating in an inert polar solvent such as DMF, DMSO, THF, toluene with or without the presence of a catalyst such as tetrabutylammonium iodide and the such like, to yield the compound 15. Again displacement of the Weinreb amide with an organolithium species completes the synthesis of a ketone suitable for cyclization under the Fischer condition described above for indole synthesis.

solvent such as benzene, toluene, tetrahydrofuran or mixtures thereof to give the desired ketone 16.

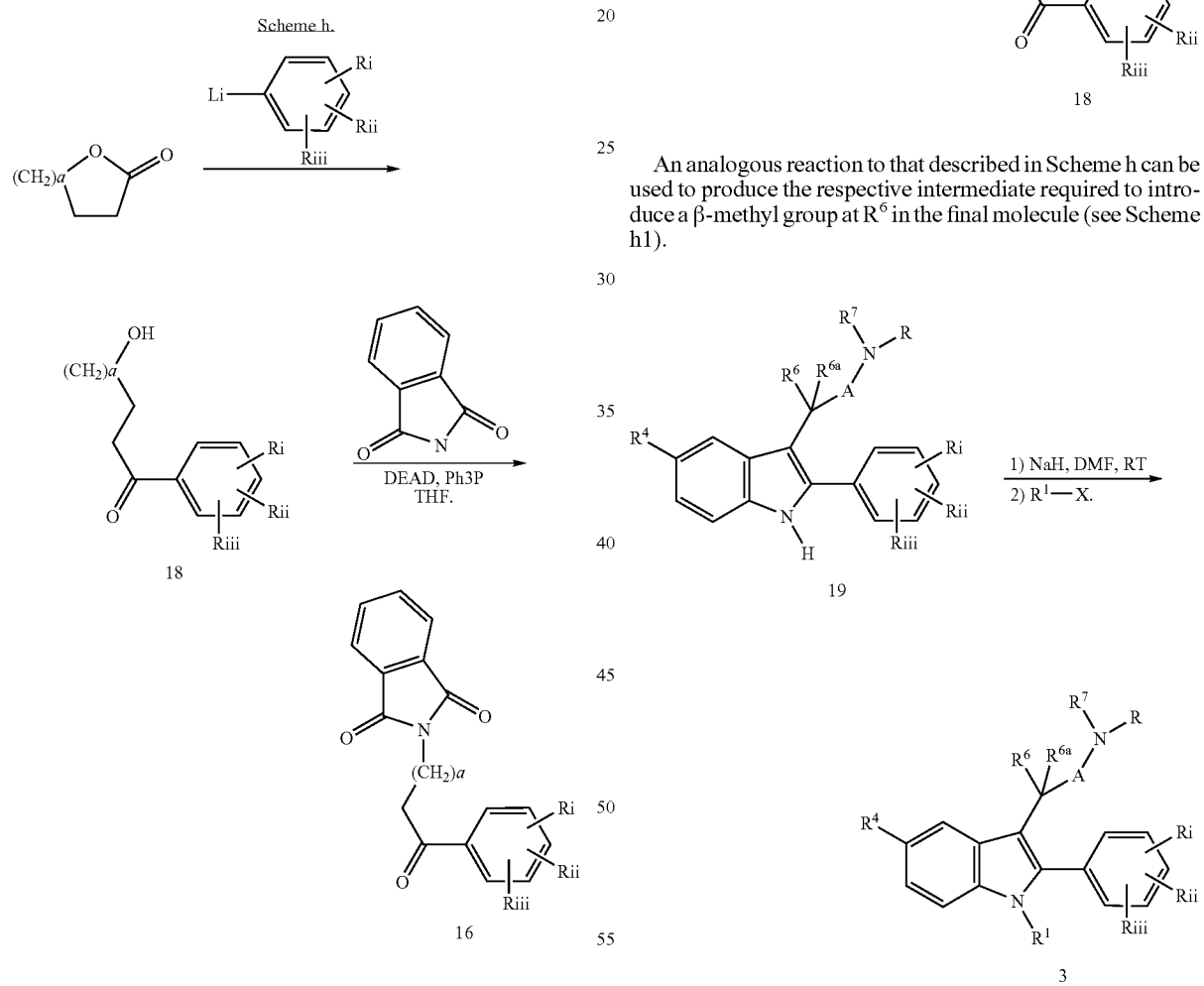

An analogous reaction to that described in Scheme h can be used to produce the respective intermediate required to introduce a β-methyl group at $R^6$ in the final molecule (see Scheme h1).

An alternative approach to a phthalimide protected nitrogen ketone, such as 16, can be taken by firstly treating a lactone, with an organolithium species as in the above schemes in a suitable solvent such as THF or ether at a low temperature of between −100° C. and −50° C. to yield a primary alcohol 18 (Scheme h). The hydroxyl function of 18 is replaced with a phthalimide group by a Mitsunobu reaction with an activating agent such as diethylazodicarboxylate (DEAD), diisopropylazodicarboxylate or the like with triphenylphosphine, tri-butylphosphine and the like, in an inert If the group $R^1$ was not present on the starting hydrazine before cyclization to form an indole it may be added post cyclization by an alkylation reaction (19→3). The indole is de-protonated by a strong base, such as sodium hydride, n-butyl lithium, lithium diisopropylamine, sodium hydroxide, potassium tert-butoxide in a suitable inert solvent such as THF, DMF, DMSO and the such like, and an alkyl halide added and the mixture stirred at a temperature between 0° C. and room temperature.

Scheme i
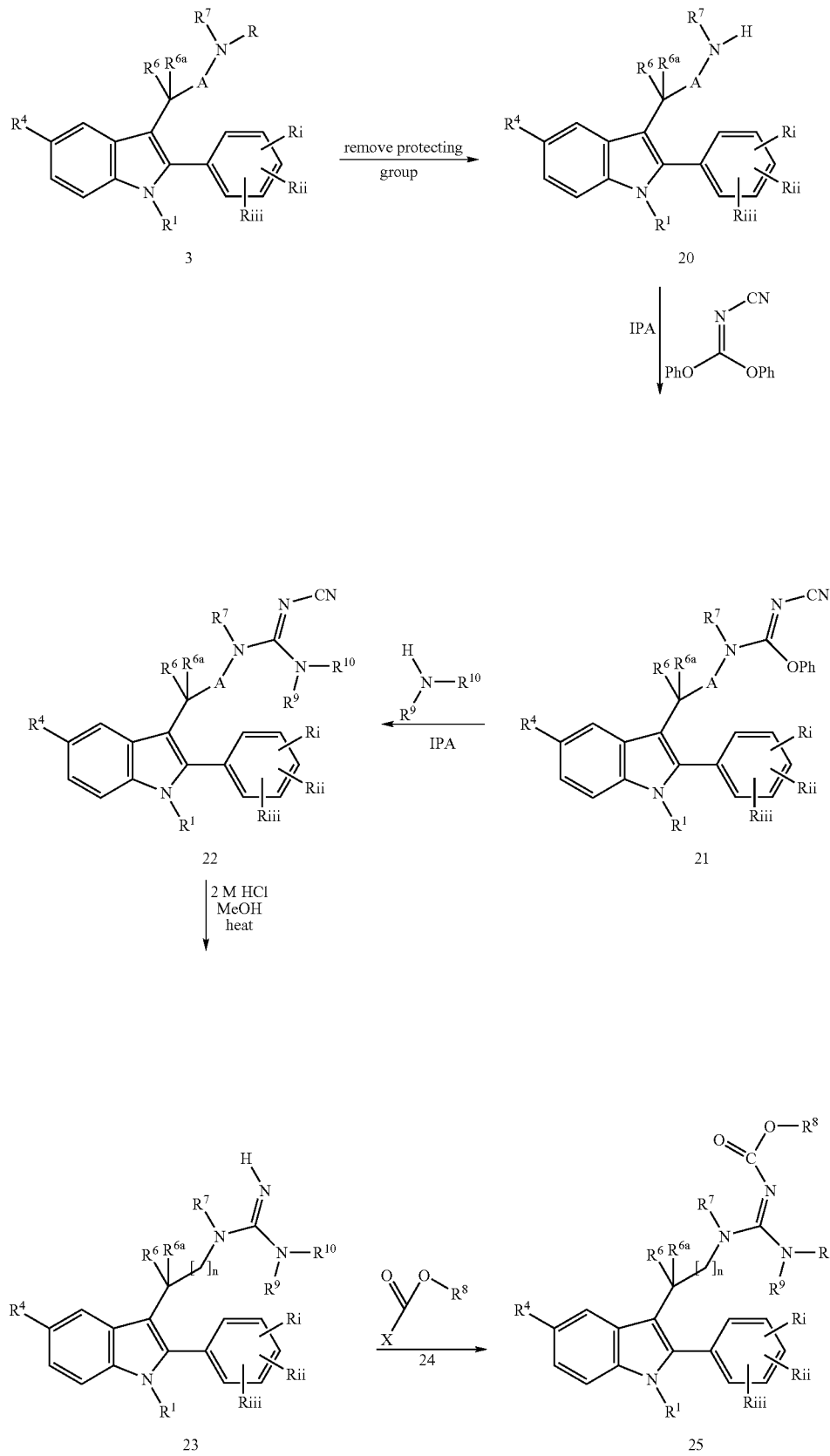

Depending on the route used above a tryptamine 20 suitable for conversion to a cyano-guandine can be formed by removal of the protecting group, for example if a tert-butylcarbamate group was used then removal is accomplished using a strong acid, for example trifluoroacetic acid or hydrochloric acid in an inert solvent such as methylene chloride, chloroform, THF or dioxane at a temperature between −20° C. and 25° C. A phthalimide group, for example, can be removed by hydrazine in a suitable solvent for example methanol, ethanol, methylene chloride, chloroform, THF dioxane at a temperature between −20° C. and 25° C. The primary amine 20 can be converted to a cyano-guanidine 22 by the two step process of reaction with diphenyl cyanocarbonimidate in an inert organic solvent such as isoproplyl alcohol, methylene chloride, chloroform, benzene, tetrahydrofuran and the like, at a temperature between −20° C. and 50° C., followed by condensation with an appropriately substituted amine in an inert organic from the list above, with heating at a temperature between −20° C. and 100° C. (Scheme I 20→21→22). Further treatment of 22 with 2 molar Hydrochloric acid in methanol at elevated temperature yields guanidine compounds 23. 23 can then be reacted with a compound 24 wherein X is a leaving group such as p-nitrophenol, at a temperature of about 0° C. in a suitable solvent such as DMF to form a compound 25.

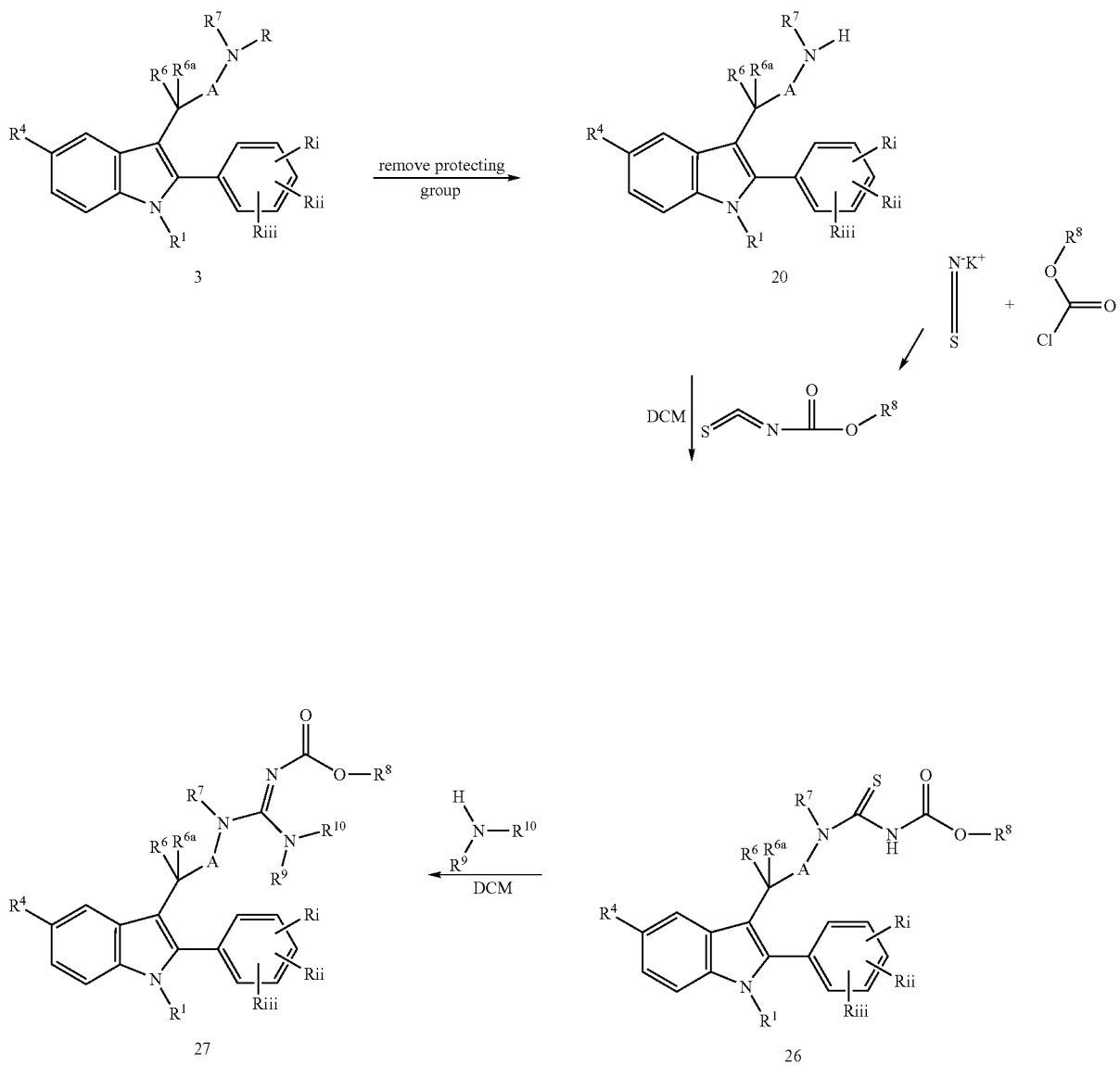

Scheme j

Alternatively, an alkyl chloroformate can be reacted with a solution of potassium thiocyanate in toluene/acetonitrile at about room temperature. The product of this reaction can then be reacted with tryptamine 20, in dichloromethane (DCM) at 0° C. to form 26. 26 can then be converted to 27 by reacting with the appropriate primary or secondary amine in the presence of EDC/DIPEA in dichloromethane at a temperature of about 0° C.

EXAMPLES

The invention will now be illustrated with the following non-limiting Examples in which, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Keiselgel: Art.9385);

(vii) isolute™ refers to silica ($SiO_2$) based columns with irregular particles with an average size of 50 μm with nominal 60 Å porosity [Source: Jones Chromatography, Ltd., Glamorgan, Wales, United Kingdom].

Abbreviations
brine a saturated solution of sodium chloride in distilled water
DCC 1,3-dicyclohexylcarbodiimide
DCM dichloromethane
DEAD diethylazodicarboxylate
DIPEA di-isopropylethylamine
DMSO Dimethyl sulphoxide
DMF dimethylformamide
EDC 1-(3-dimethylaminopropyl)-3-ethylcarbodiimide hydrochloride
HOBt 1-hydroxybenotriazole
THF tetrahydrofuran Example 1

Ethyl(1E-({2-[5-(1,1-dimethyl-2-oxo-2-pyrrolidin-1-ylethyl)-2-(3,5-dimethylphenyl)-1H-indol-3-yl]ethyl}amino)(3-pyridin-4-ylpyrrolidin-1-yl)methylidenecarbamate

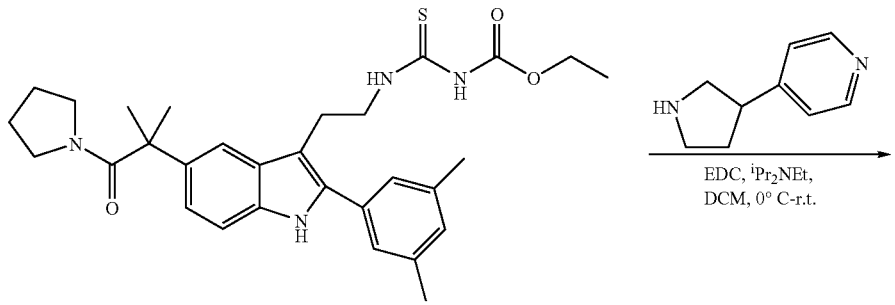

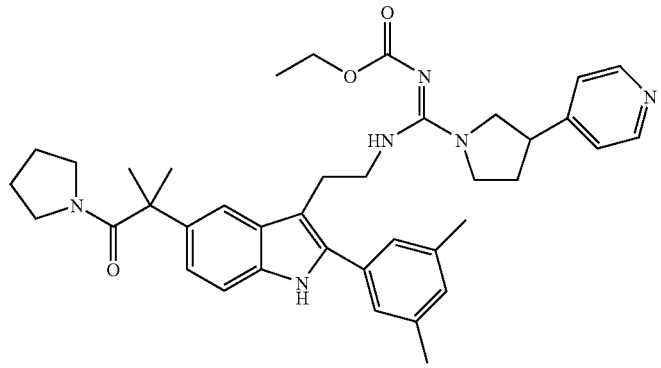

Examples 1

To a stirred, cooled (0° C.) solution of 5 (72 mg, 0.13 mmol), 4-pyrrolidin-3-yl pyridine (30 mg, 0.20 mmol) and N,N-diisopropylethylamine (46 μl, 0.26 mmol) in DCM (3 ml) was added EDC (52 mg, 0.27 mmol). After stirring for 1 hour at 0° C., the reaction mixture was stirred at ambient temperature for 16 hours. The reaction was quenched by the addition of sodium bicarbonate (3 ml, sat. aq.) and the phases were separated. The aqueous phase was extracted with DCM (2×5 ml), and the combined organic layers were dried over MgSO₄ and concentrated in vacuo. The crude product was purified by chromatography on SiO₂, eluting with a gradient 4-8% MeOH/DCM to give 8 as a yellow foam (20 mg).

Mass Spectrum m/e 649.3 (M⁺+H).

NMR Spectrum (CDCl3, δ values) 1.28 (t, 3H), 1.47-1.79 (m, 10H), 1.88 (m, 1H), 2.19 (m, 1H), 1.35 (s, 6H), 2.76 (m, 2H), 3.13-3.42 (m, 6H), 3.44-3.59 (m, 4H), 3.62 (dd, 1H), 4.08 (q, 2H), 6.98 (s, 1H), 7.05 (m, 3H), 7.15 (s, 2H), 7.30 (d, 1H), 7.45 (s, 1H), 8.23 (s, 1H), 8.50 (d, 2H).

Starting materials were prepared as described in Scheme 1 below.

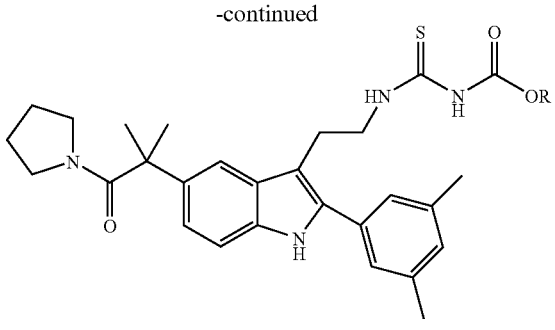

(5)

(1)

n-Butyl chloroformate (2 g, 14.64 mmol) was added to a stirred solution of potassium thiocyanate (7.83 g, 80.57 mmol) in toluene (25 ml) and acetonitrile (100 ml) at ambient temperature. After stirring for 3 days the reaction mixture was filtered through a pad of celite and the filtrate reduced in vacuo. The residue was triturated with DCM/iso-hexane(1:1), filtered and the filtrate reduced in vacuo. The crude product was purified by chromatography on SiO₂, eluting with DCM/iso-hexane(1:4) to give 1 as a yellow liquid (580 mg).

¹H NMR Spectrum (300Mz, CDCl3, δ values) 0.95 (m, 3H), 1.40 (m, 2H), 1.68 (m, 2H), 4.21 (t, 2H).

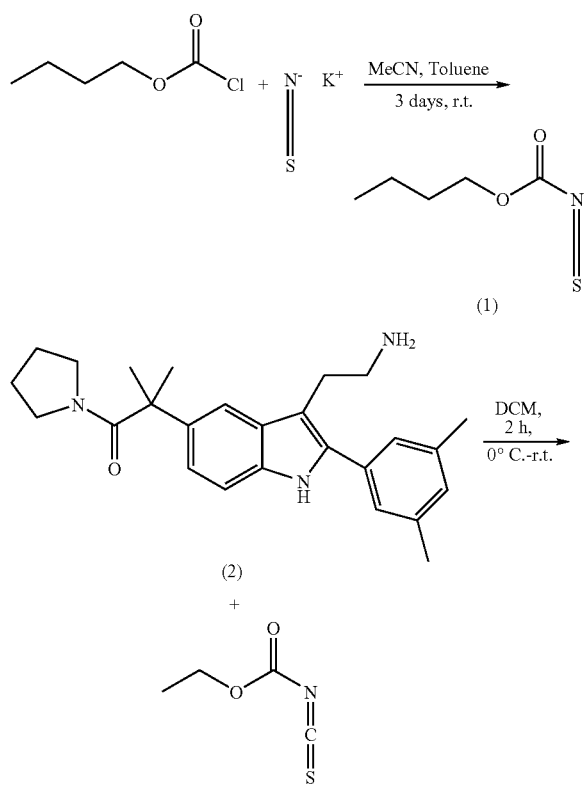

(5)

A solution of 2 (100 mg, 0.25 mmol) in DCM (3 ml) was added to a stirred, cooled (0° C.) solution of 1 (29 μl, 0.25 mmol) in DCM (2 ml) under N₂. The cooling bath was removed and stirring was continued for 2 hours. The reaction was quenched by the addition of water (3 ml) and the phases were separated. The aqueous phase was extracted with DCM (2×5 ml), and the combined organic layers were washed with brine, dried over MgSO₄ and concentrated in vacuo to give 5 as a white solid (144 mg).

Mass Spectrum m/e 535.2 (M⁺+H).

¹H NMR Spectrum (300 MHz, CDCl3, δ values) 1.20-1.36 (m, 3H), 1.48-1.83 (m, 10H), 2.40 (s, 6H), 2.80 (m, 2H), 3.28 (t, 2H), 3.55 (m, 2H), 3.95 (m, 2H), 4.08-4.24 (m, 2H), 6.99-7.09 (m, 2H), 7.20 (s, 2H), 7.24-7.35 (m, 1H), 7.65 (s, 1H), 7.97 (s, 1H), 8.20 (s, 1H), 9.70 (m, 1H).

Examples 1.1-1.2

Following a procedure similar to that described in example 1, the following examples were prepared.

| | | Mass Spectrum m/e (M⁺ + H) | NMR Spectrum (CDCl3, δ values) |
|---|---|---|---|
| 1.1 | | 661.5 | 1.25 (m, 6H), 1.54 (m, 2H), 1.56-1.74 (m, 8H), 1.88 (m, 1H), 2.18 (m, 1H), 2.35 (s, 6H), 2.76 (m, 2H), 3.12-3.40 (m, 6H), 3.42-3.58 (m, 4H), 3.63 (dd, 1H), 4.85 (m, 1H), 6.96 (s, 1H), 7.04 (d, 3H), 7.15 (s, 2H), 7.30 (d, 1H), 7.45 (s, 1H), 8.35 (s, 1H), 8.50 (d, 2H). |

| | Mass Spectrum m/e (M⁺ + H) | NMR Spectrum (CDCl3, δ values) |
|---|---|---|
| 1.2 <br> (structure) | 675.5 | 0.93 (t, 3H), 1.20-1.45 (m, 4H), 1.46-1.75 (m, 10H), 1.89 (m, 1H), 2.19 (m, 1H), 2.34 (s, 6H), 2.76 (m, 2H), 3.12-3.40 (m, 6H), 3.43-3.69 (m, 5H), 4.02 (m, 2H), 6.98 (s, 1H), 7.06 (d, 3H), 7.17 (s, 2H), 7.30 (m, 1H), 7.46 (s, 1H), 8.40 (s, 1H), 8.51 (d, 2H). |

Example 2 isopropyl [(1E)-({(2S)-2-[5-[2-(2-azabicyclo[2.2.2]oct-2-yl)-1,1-dimethyl-2-oxoethyl]-2-(3,5-dimethylphenyl)-1H-indol-3-yl]propyl}amino)(3-pyridin-4-ylpyrrolidin-1-yl)methylene]carbamate

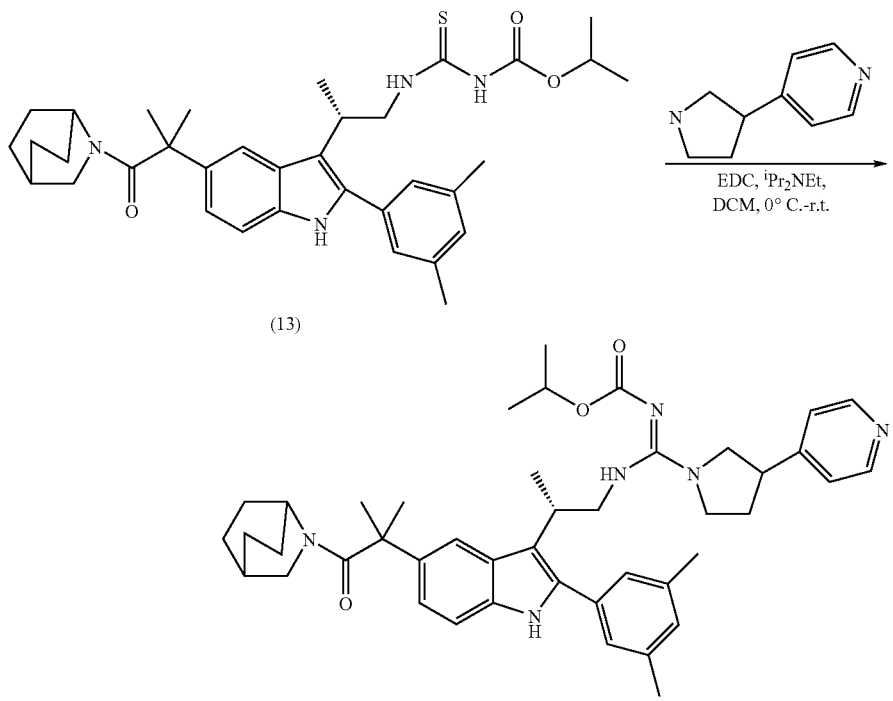

To a stirred, cooled (0° C.) solution of 13 (543 mg, 1.06 mmol), 4-pyrrolidin-3-yl pyridine (200 mg, 1.35 mmol) and N,N-diisopropylethylamine (188 μl, 1.08 mmol) in DCM (15 ml) was added EDC (173 mg, 0.90 mmol). After stirring for 16 hours at ambient temperature in the dark, the reaction mixture was cooled (0° C.) and further N,N-diisopropylethylamine (94 μl, 0.54 mmol) and EDC (86 mg, 0.45 mmol) were added. The reaction mixture was stirred for 30 min at 0° C. and 4 hours at ambient temperature. The reaction was quenched by the addition of water (15 ml) and the phases were separated. The aqueous phase was extracted with DCM (2×10 ml), and the combined organic layers were washed with brine (10 ml, sat. aq.), dried over MgSO₄ and concentrated in vacuo. The crude product was purified by chromatography on SiO₂, eluting with a gradient of 5-7% MeOH/DCM to give Example 2 as a yellow foam (266 mg).

Mass Spectrum m/e 715.3 (M⁻–H).

NMR Spectrum (CDCl3, δ values) 1.20-1.39 (m, 10H), 1.40-1.70 (m, 14H), 1.72-1.93 (m, 1H), 2.14 (m, 1H), 2.35 (s, 6H), 3.20-3.70 (m, 11H), 4.83 (m, 1H), 6.95-7.10 (m, 6H), 7.32 (d, 1H), 7.48 (s, 1H), 8.02 (s, 1H), 8.50 (d, 2H).

Starting materials were prepared as described in Scheme 2 below.

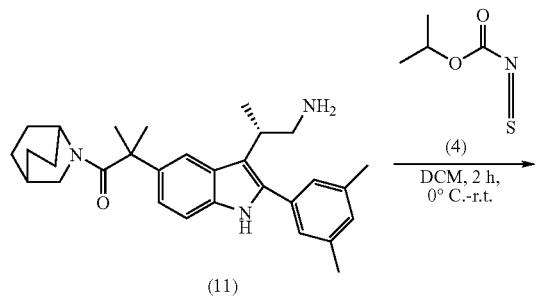

(11)

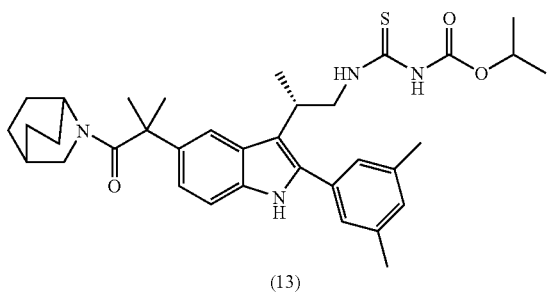

(13)

A solution of 11 (412 mg, 0.90 mmol) in DCM (7 ml) was added to a stirred, cooled (0° C.) solution of 4 (131 mg, 0.90 mmol) in DCM (8 ml) under $N_2$. The cooling bath was removed and stirring was continued for 2 hours. The reaction was quenched by the addition of water (10 ml) and the phases were separated. The aqueous phase was extracted with DCM (2×10 ml), and the combined organic layers were washed with brine, dried over $MgSO_4$ and concentrated in vacuo to give 13 as a yellow solid (573 mg).

Mass Spectrum m/e 603.3 ($M^+$+H).

NMR Spectrum (CDCl3, δ values) 1.18-1.67 (m, 24H), 2.38 (s, 6H), 3.45 (s, 2H), 3.55 (m, 1H), 4.00 (m, 1H), 4.14 (m, 2H), 4.86 (m, 1H), 7.01-7.10 (m, 2H), 7.14 (s, 2H), 7.32 (d, 1H), 7.56 (s, 1H), 7.73 (s, 1H), 7.96 (s, 1H), 9.55 (m, 1H).

Example 2.1

Following a procedure similar to that described in Example 2, the following example was prepared.

| | | Mass Spectrum m/e (M⁻H) | NMR Spectrum (CDCl3, δ values) |
|---|---|---|---|
| 2.1 | 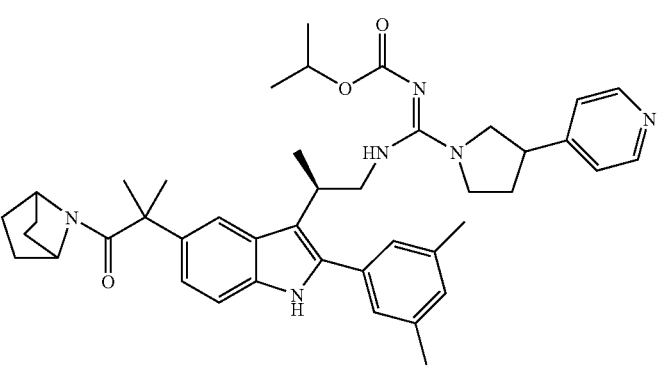 | 701.2 | 1.00-1.40 (m, 10H), 1.42-1.95 (m, 14H), 2.15 (m, 1H), 2.35 (s, 6H), 3.20-3.80 (m, 9H), 4.55-4.90 (m, 2H), 6.99-7.12 (m, 5H), 7.15 (d, 1H), 7.32 (d, 1H), 7.55 (s, 1H), 8.05 (s, 1H), 8.50 (d, 2H). |

Example 3

Isopropyl(1E)-({2-[5-(1,1-dimethyl-2-oxo-2-(N,N-diethylamino)ethyl)-2-(3,5-dimethylphenyl)-1H-indol-3-yl]ethyl}amino)(3-pyridin-4-ylpyrrolidin-1-yl)methylidenecarbamate

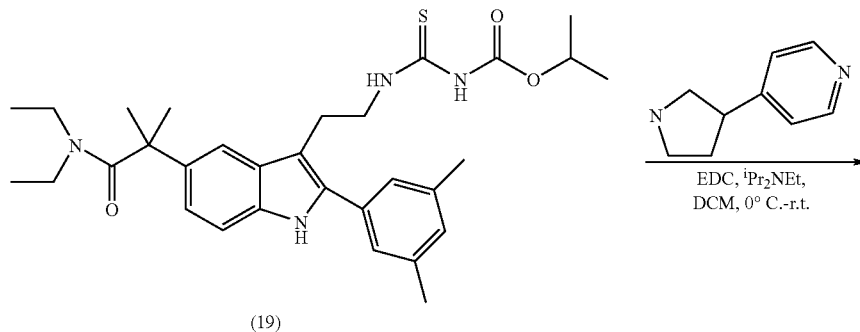

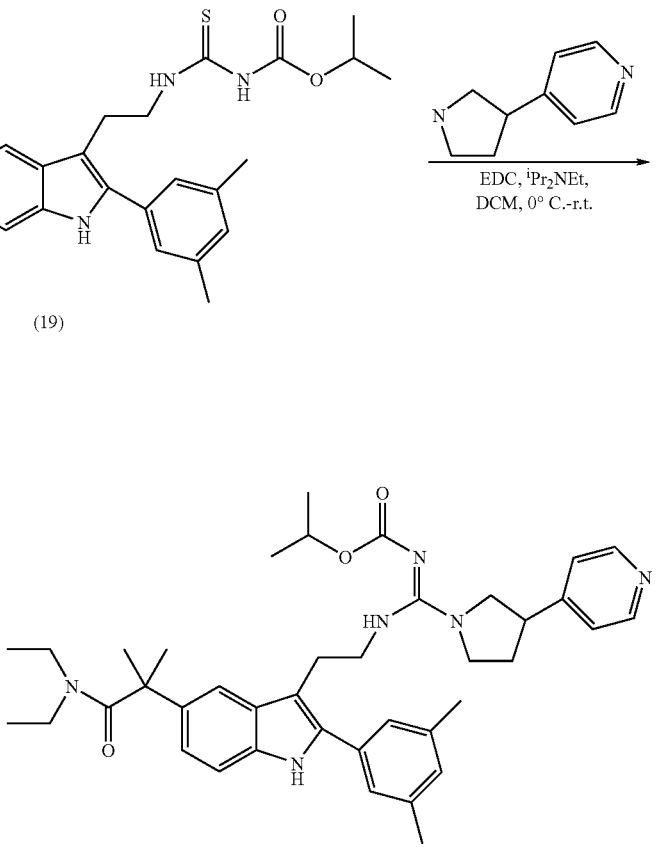

Example 3

To a stirred, cooled (0° C.) solution of 19 (584 mg, 1.06 mmol), 4-pyrrolidin-3-yl pyridine (236 mg, 1.59 mmol) and N,N-diisopropylethylamine (277 μl, 1.59 mmol) in DCM (15 ml) was added EDC (204 mg, 1.06 mmol). After stirring for 16 hours at ambient temperature in the dark, the reaction mixture was cooled (0° C.) and further N,N-diisopropylethylamine (185 μl, 1.06 mmol) and EDC (102 mg, 0.53 mmol) were added. The reaction mixture was stirred for 30 minutes at 0° C. and 4 hours at ambient temperature. The reaction was quenched by the addition of water (15 ml) and the phases were separated. The aqueous phase was extracted with DCM (2×10 ml), and the combined organic layers were washed with brine (10 ml, sat. aq.), dried over MgSO$_4$ and concentrated in vacuo. The crude product was purified by chromatography on SiO$_2$, eluting with a gradient of 5-7% MeOH/DCM to give 21 as a pale yellow foam (420 mg).

Mass Spectrum m/e 663.4 (M$^-$–H)

NMR Spectrum (CDCl3, δ values) 0.70 (m, 3H), 1.13 (m, 3H), 1.26 (dd, 6H), 1.60 (s, 6H), 1.88 (m, 1H), 2.18 (m, 1H), 2.34(s, 6H), 2.92 (m, 2H), 3.13-3.44 (m, 8H), 3.50 (m, 2H), 3.63 (dd, 1H), 4.85 (m, 1H), 6.96 (s, 1H), 7.04 (d, 3H), 7.16 (s, 2H), 7.30 (d, 1H), 7.41 (s, 1H), 8.30 (s, 1H), 8.50 (d, 2H).

Starting materials were prepared as described in Scheme 3 below.

Scheme 3

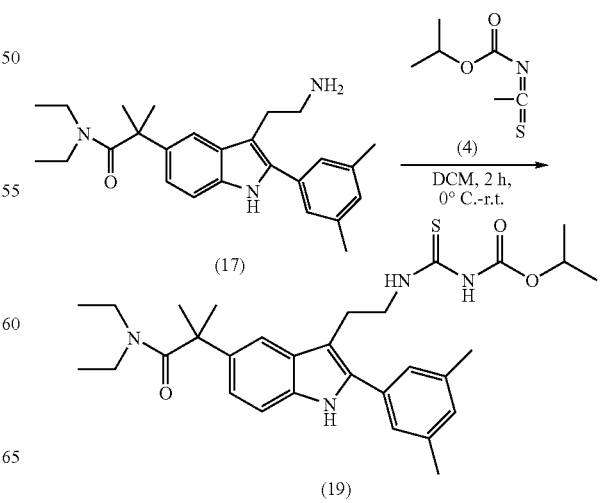

(19)

A solution of 17 (190 mg, 0.47 mmol) in DCM (7 ml) was added to a stirred, cooled (0° C.) solution of 4 (68 mg, 0.47 mmol) in DCM (3 ml) under $N_2$. The cooling bath was removed and stirring was continued for 2 hours. The reaction was quenched by the addition of water (10 ml) and the phases were separated. The aqueous phase was extracted with DCM (2×10 ml), and the combined organic layers were washed with brine, dried over $MgSO_4$ and concentrated in vacuo to give 19 as a yellow solid (260 mg).

Mass Spectrum m/e 551.2 ($M^+$+H).

NMR Spectrum (CDCl3, δ values) 0.71 (m, 3H), 1.13 (m, 3H), 1.27 (d, 6H), 1.63 (s, 6H), 2.40 (s, 6H), 2.95 (m, 2H), 3.26(t, 2H), 3.36 (m, 2H), 3.95 (m, 2H), 4.90 (m, 1H), 7.00-7.06 (m, 2H), 7.20 (s, 2H), 7.30 (d, 1H), 7.61 (s, 1H), 7.83 (s, 1H), 8.07 (s, 1H), 9.72 (m, 1H).

Example 3.1

Following a procedure similar to that described in Example 3, the following example was prepared.

| | | Mass Spectrum m/e (M⁻H) | NMR Spectrum (CDCl3, δ values) |
|---|---|---|---|
| 3.1 | | 687.3 | 1.00-1.80 (m, 8H), 1.27 (d, 6H), 1.60 (d, 6H), 1.90 (m, 1H), 2.20 (m, 1H), 2.35 (s, 6H), 3.14-3.80 (m, 10H), 4.60-4.80 (m, 1H), 4.85 (m, 1H), 6.99 (s, 1H), 7.05 (d, 2H), 7.10-7.19 (m, 3H), 7.30 (d, 1H), 7.49 (s, 1H), 8.10 (s, 1H), 8.54 (d, 2H). |

Example 4

Isopropyl(1E)-({2-[5-[2-(N,N-diethylamino)-1,1-dimethyl-2-oxoethyl]-2-(3,5-dimethylphenyl)-1H-indol-3-yl]ethyl}amino)(4-methylpiperazin-1-yl)methylidenecarbamate

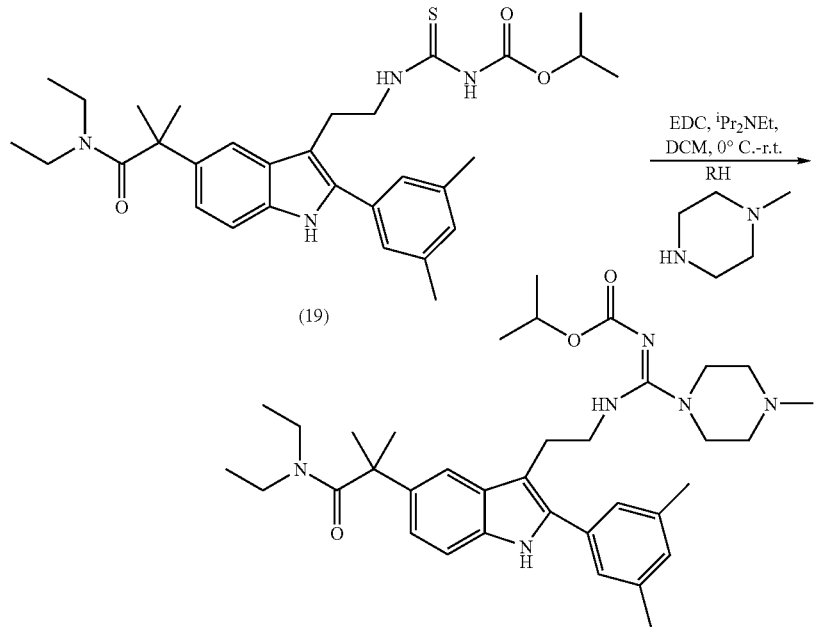

Example 4

To a stirred, cooled (0° C.) solution of 19 [see Example 3] (217 mg, 0.39 mmol), N-methylpiperazine (66 μl, 0.59 mmol) and N,N-diisopropylethylamine (82 μl, 0.47 mmol) in DCM (4 ml) was added EDC (76 mg, 0.40 mmol). After stirring for 16 hours at ambient temperature, the reaction mixture was cooled (0° C.) and further N,N-diisopropylethylamine (41 μl, 0.24 mmol) and EDC (38 mg, 0.20 mmol) were added. The reaction mixture was stirred for 30 minutes at 0° C. and 4 hours at ambient temperature. The reaction was quenched by the addition of water (10 ml) and the phases were separated. The aqueous phase was extracted with DCM (2×10 ml), and the combined organic layers were washed with brine (5 ml, sat. aq.), dried over MgSO$_4$ and concentrated in vacuo. The crude product was purified by chromatography on SiO$_2$, eluting with a gradient of 2-10% MeOH/DCM to give 23 as a white solid (130 mg).

Mass Spectrm m/e 617.5 (M$^+$+H).

NMR Spectrum (CDCl3, δ values) 0.74 (m, 3H), 1.15 (m, 3H), 1.28 (d, 6H), 1.62 (s, 6H), 2.23 (s, 3H), 2.27 (t, 4H), 2.40 (s, 6H), 2.93 (m, 2H), 3.19 (m, 2H), 3.25 (t, 4H), 3.39 (m, 4H), 4.86 (m, 1H), 7.05 (m, 2H), 7.15 (s, 2H), 7.32 (d, 1H), 7.43 (s, 1H), 8.05 (s, 1H), 8.19 (m, 1H).

Examples 4.1-4.2

Following a procedure similar to that described in Example 4, the following examples were prepared.

| | | Mass Spectrum m/e (M$^+$ + H) | NMR Spectrum (CDCl3, δ values) |
|---|---|---|---|
| 4.1 | | 627.3 | 0.72 (m, 3H), 1.14 (s, 3H), 1.27 (d, 6H), 1.55-1.70 (m, 8H), 1.78 (m, 2H), 2.40 (s, 6H), 2.70 (m, 1H), 2.93 (m, 2H), 3.02-3.24 (m, 4H), 3.38 (m, 6H), 4.86 (m, 1H), 7.07 (m, 2H), 7.15 (s, 2H), 7.33 (d, 1H), 7.40 (s, 1H), 8.14 (s, 1H), 8.35 (s, 1H). |
| 4.2 | | 601.8 | 0.74 (m, 3H), 1.14 (m, 3H), 1.25 (d, 6H), 1.49 (m, 2H), 1.60 (s, 6H), 2.10 (m, 2H), 2.38 (s, 6H), 2.83-3.10 (m, 4H), 3.18 (t, 2H), 3.38 (m, 2H), 3.54 (m, 2H), 4.85 (m, 1H), 7.03 (s, 1H), 7.09 (d, 1H), 7.16 (s, 2H), 7.35 (d, 1H), 7.43 (s, 1H), 8.19 (s, 1H). |

Example 5

(5-Methyl-2-oxo-1,3-dioxol-4-yl)methyl(1E)-({2-[5-[2-(diethylamino)-1,1-dimethyl-2-oxoethyl]-2-(3,5-dimethylphenyl)-1H-indol-3-yl]ethyl}amino)(3-pyridin-4-ylpyrrolidin-1-yl)methylidenecarbamate

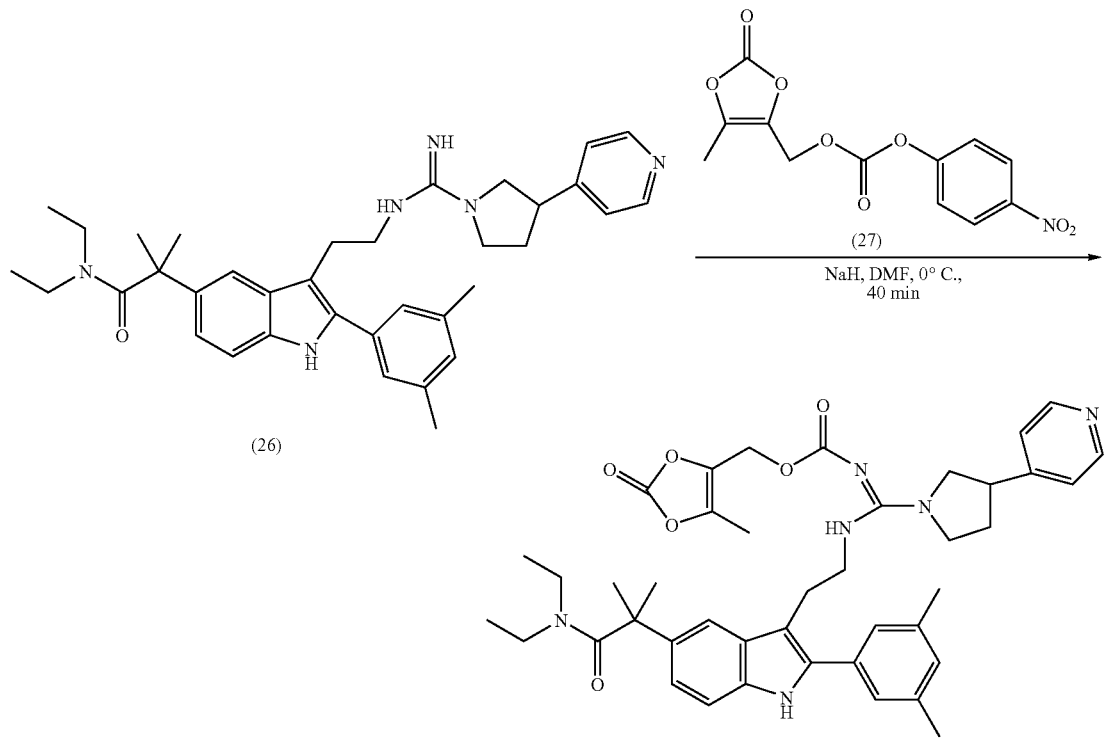

To a cooled (0° C.), stirred solution of (26) (118 mg, 0.19 mmol) in DMF (3 ml), under $N_2$, was added NaH (16 mg, 0.40 mmol). After stirring for 30 minutes, a solution of 27 (62 mg, 0.21 mmol) in DMF (2 ml) was added dropwise. The reaction mixture was stirred at 0° C. for 4 hours and left to stand at −20° C. for 16 hours. The reaction was quenched by the addition of water (15 ml) and then extracted with EtOAc (3×10 ml). The combined organic layers were washed with brine (10 ml sat. aq.), dried over $MgSO_4$ and concentrated in vacuo. The crude product was purified by chromatography on $SiO_2$, eluting with a gradient of 2-10% MeOH/DCM to give 28 as a yellow solid (45 mg).

Mass Spectrum m/e 733.3 (M⁻−H).

NMR Spectrum (CDCl3, δ values) 0.73 (m, 3H), 1.14 (m, 3H), 1.60 (s, 6H), 1.90 (m, 1H), 2.10 (s, 3H), 2.22 (m, 1H), 2.35 (s, 6H), 2.90 (m, 2H), 3.14-3.62 (m, 11H), 4.79 (s, 2H), 6.99 (s, 1H), 7.00-7.12 (m, 3H), 7.17 (s, 2H), 7.34 (d, 1H), 7.41 (s, 1H), 8.05 (s, 1H), 8.54 (m, 2H).

Example 6

2-[({[(1E)-({(2S)-2-[5-[2-(2-azabicyclo[2.2.2]oct-2-yl)-1,1-dimethyl-2-oxoethyl]-2-(3,5-dimethylphenyl)-1H-indol-3-yl]propyl}amino)(3-pyridin-4-ylpyrrolidin-1-yl)methylene]amino}carbonyl)oxy]-2-methylpropyl acetate

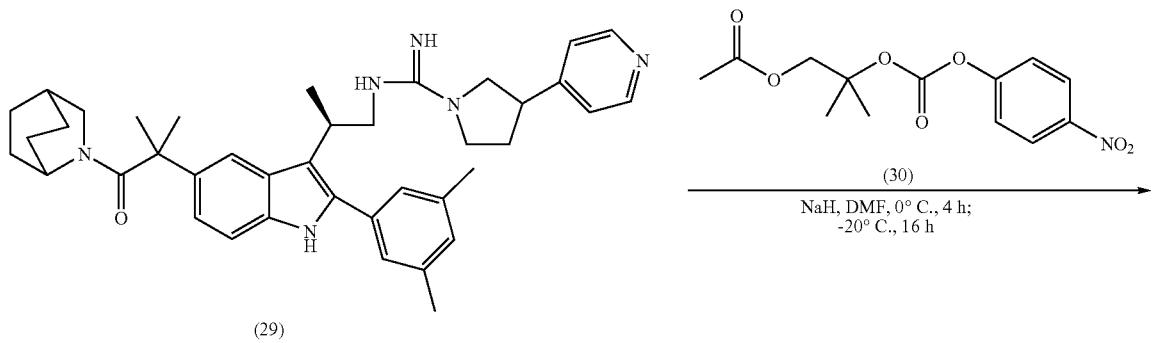

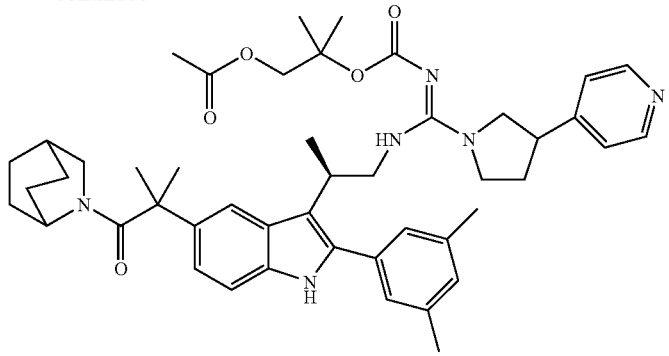

Example 6

To a cooled (0° C.), stirred solution of (29) (50 mg, 74.9 μmol) in DMF (2 ml), under $N_2$, was added NaH (7 mg, 0.16 mmol). After stirring for 30 minutes a solution of (30) (67 mg, 0.23 mmol) in DMF (2 ml) was added dropwise. The reaction mixture was stirred at 0° C. for 40 minutes. The reaction was quenched by the addition of water (15 ml) and then extracted with EtOAc (3×10 ml). The combined organic layers were washed with brine (10 ml sat. aq.), dried over $MgSO_4$ and concentrated in vacuo. The crude product was purified by chromatography on $SiO_2$, eluting with a gradient of 5-10% MeOH/DCM to give 31 as a yellow solid (10 mg).

Mass Spectrum m/e 789.3 ($M^+$+H).

NMR Spectrum (CDCl3, δ values) 1.10-1.70 (m, 24H), 1.75-1.90 (m, 1H), 2.00 (s, 3H), 2.15-2.30 (m, 1H), 2.30 (s, 6H), 3.17 (m, 1H), 3.28-4.00 (m, 12H), 6.86 (s, 2H), 6.95-7.15 (m, 3H), 7.20-7.30 (m, 2H), 7.46 (s, 1H), 8.18 (d, 1H), 8.50 (d, 2H).

Therapeutic Uses

Compounds of Formula (I) are provided as medicaments for antagonising gonadotropin releasing hormone (GnRH) activity in a patient, eg, in men and/or women. To this end, a compound of Formula (I) can be provided as part of a pharmaceutical formulation which also includes a pharmaceutically acceptable diluent or carrier (eg, water). The formulation may be in the form of tablets, capsules, granules, powders, syrups, emulsions (eg, lipid emulsions), suppositories, ointments, creams, drops, suspensions (eg, aqueous or oily suspensions) or solutions (eg, aqueous or oily solutions). If desired, the formulation may include one or more additional substances independently selected from stabilising agents, wetting agents, emulsifying agents, buffers, lactose, sialic acid, magnesium stearate, terra alba, sucrose, corn starch, talc, gelatin, agar, pectin, peanut oil, olive oil, cacao butter and ethylene glycol.

The compound is preferably orally administered to a patient, but other routes of administration are possible, such as parenteral or rectal administration. For intravenous, subcutaneous or intramuscular administration, the patient may receive a daily dose of 0.1 $mgkg^{-1}$ to 30 $mgkg^{-1}$ (preferably, 5 $mgkg^{-1}$ to 20 $mgkg^{-1}$) of the compound, the compound being administered 1 to 4 times per day. The intravenous, subcutaneous and intramuscular dose may be given by means of a bolus injection. Alternatively, the intravenous dose may be given by continuous infusion over a period of time. Alternatively, the patient may receive a daily oral dose which is approximately equivalent to the daily parenteral dose, the composition being administered 1 to 4 times per day. A suitable pharmaceutical formulation is one suitable for oral administration in unit dosage form, for example as a tablet or capsule, which contains between 10 mg and 1 g (preferably, 100 mg and 1 g) of the compound of the invention.

Buffers, pharmaceutically acceptable co-solvents (eg, polyethylene glycol, propylene glycol, glycerol or EtOH) or complexing agents such as hydroxy-propyl β cyclodextrin may be used to aid formulation.

One aspect of the invention relates to the use of compounds according to the invention for reducing the secretion of LH and/or FSH by the pituitary gland of a patient. In this respect, the reduction may be by way of a reduction in biosynthesis of the LH and FSH and/or a reduction in the release of LH and FSH by the pituitary gland. Thus, compounds according to the invention can be used for therapeutically treating and/or preventing a sex hormone related condition in the patient. By "preventing" we mean reducing the patient's risk of contracting the condition. By "treating" we mean eradicating the condition or reducing its severity in the patient. Examples of sex, hormone related conditions are: a sex hormone dependent cancer, benign prostatic hypertrophy, myoma of the uterus, endometriosis, polycystic ovarian disease, uterine fibroids, prostatauxe, myoma uteri, hirsutism and precocious puberty. Examples of sex hormone dependent cancers are: prostatic cancer, uterine cancer, breast cancer and pituitary gonadotrophe adenoma.

The compounds of the invention may be used in combination with other drugs and therapies used to treat/prevent sex-hormone related conditions.

If formulated as a fixed dose such combination products employ the compounds of this invention within the dosage range described herein and the other pharmaceutically-active agent within its approved dosage range. Sequential use is contemplated when a combination formulation is inappropriate.

In the field of medical oncology examples of such combinations include combinations with the following categories of therapeutic agent:

i) anti-angiogenic agents (for example linomide, inhibitors of integrin αvβ3 function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrozole, vorazole, exemestane), anti-progestogens, anti-androgens (for example flutamide, nilutamide, bicalutamide, cyproterone acetate), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-folates like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

The compounds of the invention may also be used in combination with surgery or radiotherapy.

Assays

The ability of compounds according to the invention to act as antagonists of GnRH can be determined using the following in vitro assays.

Binding Assay using Rat Pituitary GnRH Receptor

The assay is performed as follows:—

1. Incubate crude plasma membranes prepared from rat pituitary tissues in a Tris.HCl buffer (pH. 7.5, 50 mM) containing bovine serum albumin (0.1%), [I-125]D-t-Bu-Ser6-Pro9-ethyl amide-GnRH, and the test compound. Incubation is at 4° C. for 90 minutes to 2 hours.

2. Rapidly filter and repeatedly wash through a glass fibre filter.

3. Determine the radioactivity of membrane bound radio-ligands using a gamma counter.

From this data, the $IC_{50}$ of the test compound can be determined as the concentration of the compound required to inhibit radio-ligand binding to GnRH receptors by 50%.

Compounds according to the present invention have activity at a concentration from 1 nM to 5 µM.

Binding Assay using Human GnRH Receptor

Crude membranes prepared from CHO cells expressing human GnRH receptors are sources for the GnRH receptor. The binding activity of compounds according to the invention can be determined as an $IC_{50}$ which is the compound concentration required to inhibit the specific binding of [$^{125}$I]buserelin to GnRH receptors by 50%. [$^{125}$I]Buserelin (a peptide GnRH analogue) is used here as a radiolabelled ligand of the receptor.

Assay to Determine Inhibition of LH Release

The LH release assay can be used to demonstrate antagonist activity of compounds, as demonstrated by a reduction in GnRH-induced LH release.

Preparation of Pituitary Glands

Pituitary glands obtained from rats are prepared as follows. Suitable rats are Wistar male rats (150-200 g) which have been maintained at a constant temperature (eg, 25° C.) on a 12 hour light/12 hour dark cycle. The rats are sacrificed by decapitation before the pituitary glands are aseptically removed to tube containing Hank's Balanced Salt Solution (HBSS). The glands are further processed by:—

1. Centrifugation at 250×g for 5 minutes;

2. Aspiration of the HBSS solution;

3. Transfer of the glands to a petri dish before mincing with a scalpel;

4. Transfer of the minced tissue to a centrifuge tube by suspending the tissue three successive times in 10 ml aliquots of HBSS containing 0.2% collagenase and 0.2% hyaluronidase;

5. Cell dispersion by gentle stirring of the tissue suspension while the tube is kept in a water bath at 37° C.;

6. Aspiration 20 to 30 times using a pipette, undigested pituitary fragments being allowed to settle for 3 to 5 minutes;

7. Aspiration of the suspended cells followed by centrifugation at 1200×g for 5 minutes;

8. Re-suspension of the cells in culture medium of DM containing 0.37% $NaHCO_3$, 10% horse serum, 2.5% foetal bovine serum, 1% non essential amino acids, 1% glutamine and 0.1% gentamycin;

9. Treatment of the undigested pituitary fragments 3 times with 30 ml aliquots of the collagenase and hyaluronidase;

10. Pooling of the cell suspensions and dilution to a concentration of $3 \times 10^5$ cells/ml;

11. Placing of 1.0 ml of this suspension in each of a 24 well tray, with the cells being maintained in a humidified 5% $CO_2$/95% air atmosphere at 37° C. for 3 to 4 days Testing of Compounds The test compound is dissolved in DMSO to a final concentration of 0.5% in the incubation medium.

1.5 hours prior to the assay, the cells are washed three times with DMEM containing 0.37% $NaHCO_3$, 10% horse serum, 2.5% foetal bovine serum, 1% non essential amino acids (100×), 1% glutamine (100×), 1% penicillin/streptomycin (10,000 units of each per ml) and 25 mM HEPES at pH 7.4. Immediately prior to the assay, the cells are again washed twice in this medium.

Following this, 1 ml of fresh medium containing the test compound and 2 nM GnRH is added to two wells. For other test compounds (where it is desired to test more than one compound), these are added to other respective duplicate wells. Incubation is then carried out at 37° C. for three hours.

Following incubation, each well is analysed by removing the medium from the well and centrifuging the medium at 2000×g for 15 minutes to remove any cellular material. The supernatant is removed and assayed for LH content using a double antibody radio-immuno assay. Comparison with a suitable control (no test compound) is used to determine whether the test compound reduces LH release. Compounds according to the present invention have activity at a concentration from 1 nM to 5 µM.

The invention claimed is:

1. A compound of Formula (I),

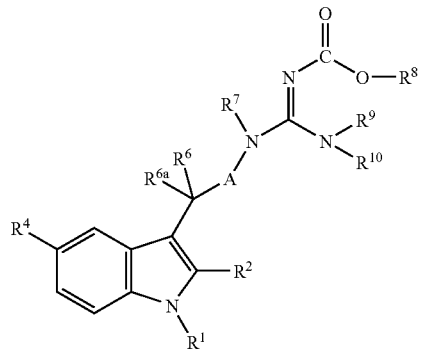

Formula (I)

wherein

A represents a direct bond or optionally substituted $C_{1-5}$alkylene;

$R^1$ represents hydrogen; optionally substituted $C_{1-8}$alkyl; or $(CH_2)_b$—$R^a$, wherein $R^a$ represents $C_{3-8}$cycloalkyl and b is zero or an integer from 1 to 6;

$R^2$ represents an optionally substituted mono- or bi-cyclic aromatic ring structure wherein the optional substituents are selected from cyano, $NR^3R^{3a}$, optionally substituted $C_{1-8}$alkyl, optionally substituted $C_{1-8}$alkoxy or halo;

$R^3$ and $R^{3a}$ are independently selected from hydrogen; optionally substituted $C_{1-8}$alkyl and optionally substituted aryl;

$R^4$ is selected from an optionally substituted 3- to 8-membered heterocyclic ring containing from 1 to 4 heteroatoms independently selected from O, N and S; or a group of formula III-a; III-b; III-c; III-d; III-e; III-f, III-g, III-h, III-i, III-j or III-k;

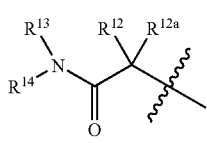

III-a

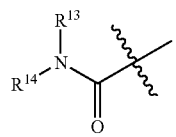

III-b

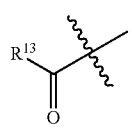

III-c

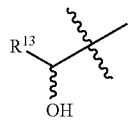

III-d

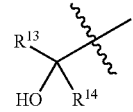

III-e

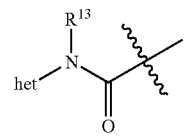

III-f

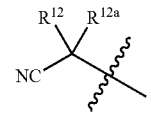

III-g

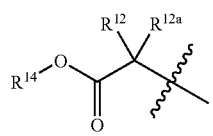

III-h

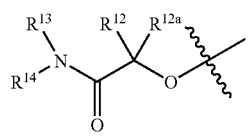

III-i

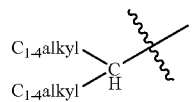

III-j

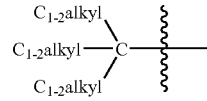

III-k

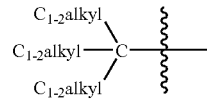

III-k wherein het represents an optionally substituted 3- to 8-membered heterocyclic ring containing from 1 to 4 heteroatoms independently selected from O, N and S;

$R^6$ and $R^{6a}$, are selected from:

(i) $R^6$ and $R^{6a}$ are independently selected from hydrogen and optionally substituted $C_{1-8}$alkyl; or (ii) $R^6$ and $R^{6a}$ together represent carbonyl; or (iii)

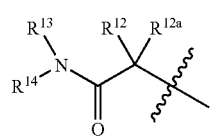

III-a

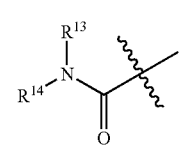

III-b

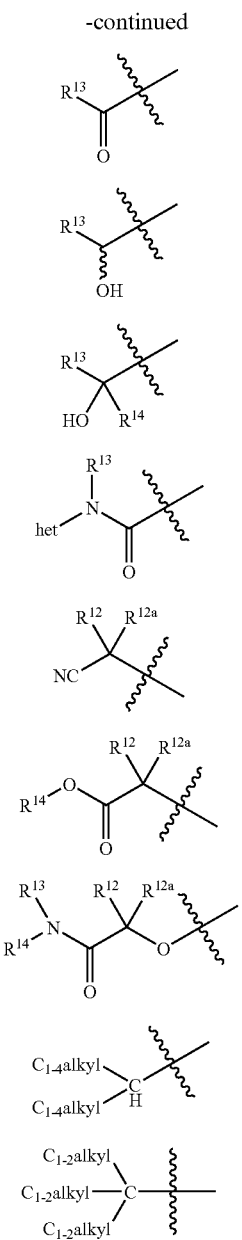

represents an optionally substituted 3- to 8-membered heterocyclic ring containing from 1 to 3 further heteroatoms independently selected from O, N and S, and $R^{6a}$ represents hydrogen and optionally substituted $C_{1-8}$alkyl;

$R^7$ represents hydrogen or optionally substituted $C_{1-8}$alkyl;

$R^8$ are selected from: $C_{1-4}$alkyl, $C_{2-4}$alkenyl, $C_{2-4}$alkynyl and heterocyclyl wherein $R^8$ is optionally substituted with halo, hydroxy, amino, $NO_2$, cyano, $C_{1-4}$alkanoyloxy, N—$C_{1-4}$alkylamino, N,N-di-$C_{1-4}$alkylamino, HO—$C_{2-4}$alkyl-NH—, HO—$C_{2-4}$alkyl-N($C_{1-4}$alkyl)-, —S($O_n$)—$C_{1-4}$alkyl, —N(R)S($O_n$)—$C_{1-4}$alkyl, —S($O_n$)N(R)—$C_{1-4}$alkyl or heterocyclyl optionally substituted by $C_{1-4}$alkyl, $C_{2-4}$alkenyl or $C_{2-4}$alkynyl, wherein R is hydrogen or $C_{1-4}$alkyl;

$R^9$ selected from:
(i) $R^9$ represents hydrogen, aryl, a 3- to 10 membered heterocyclic ring or optionally-substituted $C_{1-8}$alkyl; and
(ii) the structure N($R^9R^{10}$) represents an optionally-substituted 3- to 10 membered heterocyclic ring optionally containing from 1 to 3 further heteroatoms independently selected from O, N and S;

$R^{10}$ meets the definition in option (ii) for $R^9$ above or when $R^9$ meets the definition in option (i) above $R^{10}$ represents hydrogen or optionally substituted $C_{1-8}$alkyl;

$R^{12}$ and $R^{12a}$ are selected from:
(i) $R^{12}$ and $R^{12a}$ are independently selected from hydrogen or optionally substituted $C_{1-8}$alkyl; or
(ii) $R^{12}$ and $R^{12a}$ together with the carbon to which they are attached form an optionally substituted 3 to 7-membered cycloalkyl ring;

$R^{13}$ and $R^{14}$ are selected from:
(i) $R^{13}$ is selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{14}$ is selected from hydrogen; optionally substituted $C_{1-8}$alkyl and optionally substituted aryl;
(ii) wherein $R^4$ represents a group of formula III-a, III-b or III-i, then the group $NR^{13}(—R^{14})$ represents an optionally substituted 3- to 8-membered heterocyclic ring optionally containing from 1 to 3 further heteroatoms independently selected from O, N and S; or
(iii) wherein $R^4$ represents structure III-e, $$R^{13} \diagdown N \diagup R^{14}$$

represents an optionally substituted 3- to 8-membered heterocyclic ring optionally containing from 1 to 4 heteroatoms independently selected from O, N and S;
n is 0 to 2;
or a salt, pro-drug or solvate thereof.

2. A compound according to claim 1 wherein $R^9$ represents hydrogen, optionally substituted aryl, an optionally substituted 3- to 10 membered heterocyclic ring or optionally-substituted $C_{1-8}$alkyl and $R^{10}$ represents hydrogen or optionally substituted $C_{1-8}$alkyl wherein the optional substituents on aryl, the heterocyclic ring and $C_{1-6}$alkyl are selected from: hydroxy, amino, nitro, cyano, optionally-substituted aryl, optionally substituted 3- to 8-membered heterocyclyl containing from 1 to 4 heteroatoms independently selected from O, N and S, —O—$R^b$, C(O)$NR^bR^c$, —$NR^bR^c$, —$NR^cC(O)$—$NR^bR^c$, —$NR^cS(O_{0-2})R^b$, —$S(O_{0-2})R^b$, wherein $R^b$ and $R^c$ are as in claim 1.

3. A compound according to claim 2 wherein $R^9$ is a $C_{1-6}$alkyl group substituted by pyridyl, thienyl, piperidinyl, imidazolyl, triazolyl, thiazolyl, pyrrolidinyl, piperazinyl, morpholinyl, imidazolinyl, benztriazolyl, benzimidazolyl, pyrimidinyl, pyrazinyl, pyridazinyl, oxazolyl, furanyl, pyrrolyl, 1,3-dioxolanyl or 2-azetinyl, each of which is optionally substituted.

4. A compound according to claim 1 wherein the structure N($R^9R^{10}$) represents an optionally-substituted 3- to 10 membered heterocyclic ring optionally containing from 1 to 3 further heteroatoms independently selected from O, N and S.

5. A compound according to claim 4 wherein the 3- to 10 membered heterocyclic ring is optionally substituted by one of more groups selected from $R^{15}$ wherein $R^{15}$ is selected from optionally substituted aryl, an optionally substituted 3- to 10 membered heterocyclic ring or optionally substituted $C_{1-4}$alkyl wherein the optional substituents on aryl, a heterocyclic ring or $C_{1-6}$alkyl are selected from: hydroxy, amino, nitro, cyano, optionally-substituted aryl, optionally substituted 3- to 8-membered heterocyclyl containing from 1 to 4 heteroatoms independently selected from O, N and S, and —O—$R^b$, C(O)$NR^bR^c$, —$NR^bR^c$, —$NR^cC(O)$—$R^b$, —C(O) $NR^bR^c$, —$NR^cS(O_{0-2})R^b$, —$S(O_{0-2})R^b$, wherein $R^b$ and $R^c$ are as defined in claim 1.

6. A compound according to claim 1 wherein $R^4$ is selected from a group of formula III-a, III-g, III-h, III-i, III-j or III-k:

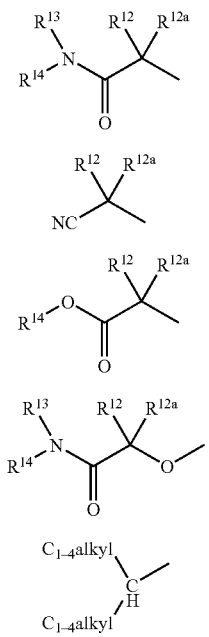

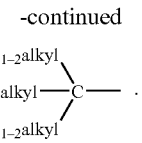

7. A compound according to claim 1 wherein X and $R^8$ represent either:—
  (a) X represents N and $R^8$ represents cyano or —C(O)O—$R^b$; or
  (b) X represents N and $R^8$ represents hydrogen.

8. A compound according to claim 1 wherein $R^2$ is selected from an optionally substituted monocyclic aromatic ring structure wherein the optional substituents are selected from cyano, $NR^eR^f$, optionally substituted $C_{1-8}$alkyl, optionally substituted $C_{1-8}$alkoxy or halo wherein $R^e$ and $R^f$ are independently selected from hydrogen, $C_{1-6}$alky or aryl.

9. A compound according to claim 1 wherein $R^1$ hydrogen.

10. A compound selected from:
  isopropyl [(1E)-({(2S)-2-[5-[2-(2-azabicyclo[2.2.2]oct-2-yl)- 1,1-dimethyl-2-oxoethyl]-2-(3,5-dimethylphenyl)-1H-indol-3-yl]propyl }amino)(3-pyridin-4-ylpyrrolidin-1-yl)methylene]carbamate; isopropyl [(1E)-({(2S)-2-[5-[2-(7-azabicyclo[2.2.1]hept-7-yl)-1,1-dimethyl-2-oxoethyl]-2-(3,5-dimethylphenyl)-1H-indol-3-yl] propyl }amino)(3-pyridin-4-ylpyrrolidin-1-yl) methylene]carbamate; and
  2-[({[(1E)-({(2S)-2-[5-[2-(2-azabicyclo[2.2.2]oct-2-yl)-1,1-dimethyl-2-oxoethyl]-2-(3,5-dimethylphenyl)-1H-indol-3-yl]propyl}amino)(3-pyridin-4-ylpyrrolidin-1-yl)methylene]amino}carbonyl)oxy]-2-methylpropyl acetate or a salt, pro-drug or solvate thereof.

11. A pharmaceutical formulation comprising a compound, or salt, pro-drug or solvate thereof, according to claim 1 and a pharmaceutically acceptable diluent or carrier.

* * * * *